(12) United States Patent
Mack et al.

(10) Patent No.: US 7,399,744 B2
(45) Date of Patent: Jul. 15, 2008

(54) METHODS FOR AFFECTING BODY COMPOSITION

(75) Inventors: Christine Marie Mack, San Diego, CA (US); Jonathan David Roth, La Jolla, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 249 days.

(21) Appl. No.: 10/851,574

(22) Filed: May 20, 2004

(65) Prior Publication Data

US 2005/0197287 A1 Sep. 8, 2005

Related U.S. Application Data

(60) Provisional application No. 60/550,447, filed on Mar. 4, 2004.

(51) Int. Cl.
*A61K 38/00* (2006.01)
(52) U.S. Cl. .................................................... 514/12
(58) Field of Classification Search ....................... None
See application file for complete search history.

(56) References Cited

U.S. PATENT DOCUMENTS

| | | | |
|---|---|---|---|
| 5,264,372 A | 11/1993 | Beaumont et al. | |
| 5,580,953 A * | 12/1996 | Albrecht et al. | 530/303 |
| 5,677,279 A | 10/1997 | Young | |
| 5,686,411 A | 11/1997 | Gaeta et al. | |
| 5,739,106 A * | 4/1998 | Rink et al. | 514/12 |
| 5,998,367 A | 12/1999 | Gaeta et al. | |
| 6,114,304 A | 9/2000 | Kolterman et al. | |
| 6,410,511 B2 | 6/2002 | L'Italien et al. | |
| 6,610,824 B2 | 8/2003 | Gaeta et al. | |
| 2003/0026812 A1 | 2/2003 | Duft et al. | |
| 2003/0092606 A1 | 5/2003 | L'Italien et al. | |
| 2004/0022807 A1 | 2/2004 | Duft et al. | |

FOREIGN PATENT DOCUMENTS

EP 0 289 287 B1 1/1998

WO WO 98/50059 11/1998

OTHER PUBLICATIONS

Bray, George, "Drug treatment of obesity", Am J. Clin Nutr 1992; 55:538S-44S.
Eiden, S., et al., "Calcitonin—a potent inhibitor of food intake in states of impaired leptin signalling in laboratory rodents", J. Physiol. 2002; 541(Pt):1041-1048.
Jung, Roland T., et al., "The management of obesity", Clinical Endocrinology 1991; 35:11-20.
Kuestner, Rolf E., "Cloning and Characterization of an Abundant Subtype of the Human Calcitonin Receptor," Mol Pharma 1994; 46:246-255.
Lee, Yann-Jinn, et al., Successful Weight Loss with Protein-Sparing Modified Fast in a Morbidly Obese Boy with . . . Clinical Pediatrics Apr. 1992; 234-236.
Lutz, T.A., et al.,"Repeated salmon calcitonin injection lowers body weight ad body fat." Scientific World Journal Dec. 18, 2001; 1(12 Sup 1):25.
Mack, C., et al., "Sustained reduction in food intake and body weight in high fat-fed rats during 28-day amylin infusion." Diabetes Jun. 2003; 52(Sup 1):A389. Abstract 1690-P.
Muff, Roman, et al., "Comparison of a CGRP and Calcitonin Receptors," Am NY Acad Sci 1992; 657:106-116.
Rushing, P.A., "Central amylin signaling and the regulation of energy homeostasis." Curr Pharm Des 2003; 9(10):819-825.
Rushing, P.A., et al., "Inhibition of central amylin signaling increases food intake and body adiposity in rates." Endocrinology 2001; 142(11):5035-5038.
Rushing. P.A., et al., "A novel action in the brain to reduce body weight." Endocrinology 2000; 141(2):850-853.
Thupari, J.N., et al., "Cronic C75 treatment of diet-induced obese mice increases fat oxidation and reduces . . . " Am J. Physiol Endocrinol Metab Jul. 2004; 287(1):E97-E104.
Fruin, et al., "Weight Loss Induced by Islet Amyloid Polypeptide(IAPP) is Not Fully Explained by Reduction in Food Intake," Digestion 1997; 58(suppl 2):55.
Mack, C et al, "Sustained reduction in food intake and body weight in high fat-fed rats during 28-day amylin infusion" Poster at ADA Meeting Jun. 2003, New Orleans, Abs 1690-P.

\* cited by examiner

*Primary Examiner*—Cecilia Tsang
*Assistant Examiner*—Thomas S. Heard
(74) *Attorney, Agent, or Firm*—Intellectual Property Group Amylin Pharmaceuticals, Inc.

(57) ABSTRACT

Methods for affecting body composition include the use of amylin or amylin agonist(s). Total body weight may be reduced, maintained or even increased; however, the body fat is reduced or body fat gain is prevented, while lean body mass is maintained or increased.

7 Claims, 20 Drawing Sheets

*P<0.05 compared to the Low Fat Diet group unless otherwise noted

*P<0.05 compared to Vehicle - High Fat Diet group

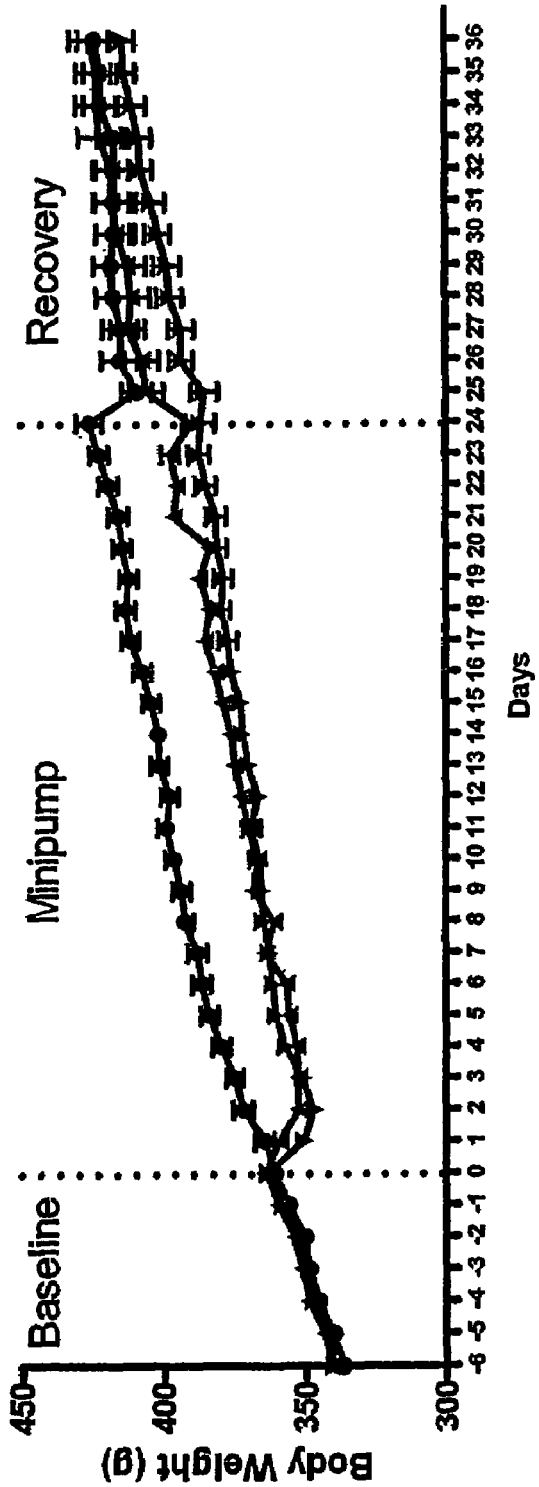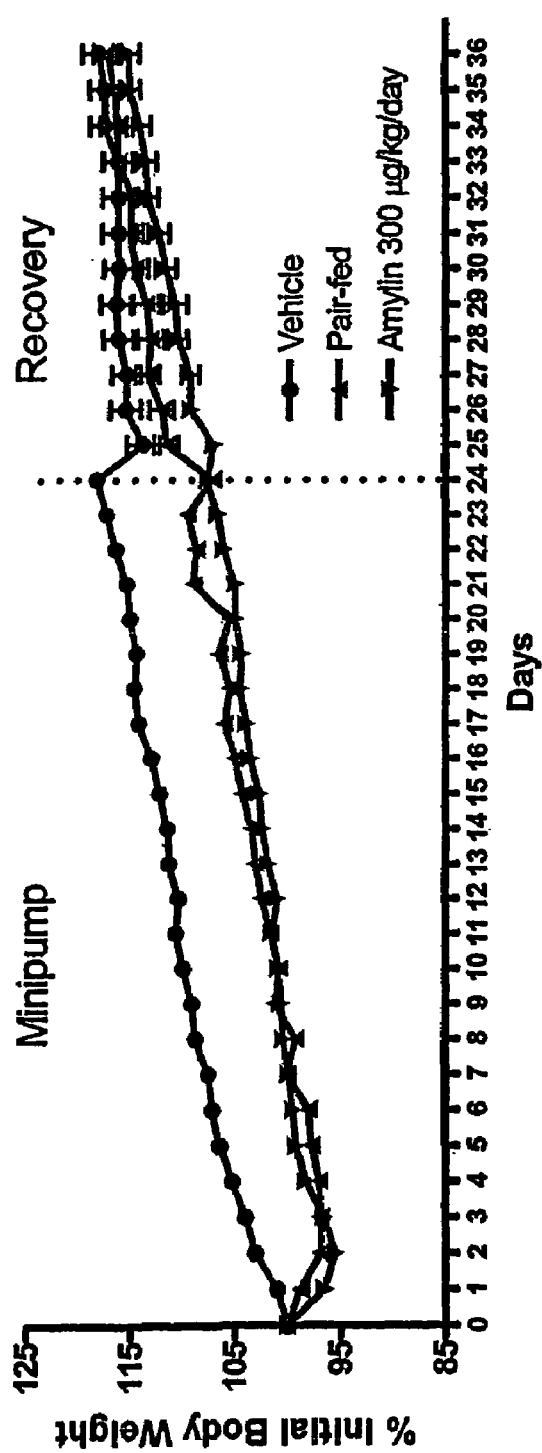
Fig. 6A
Fig. 6B

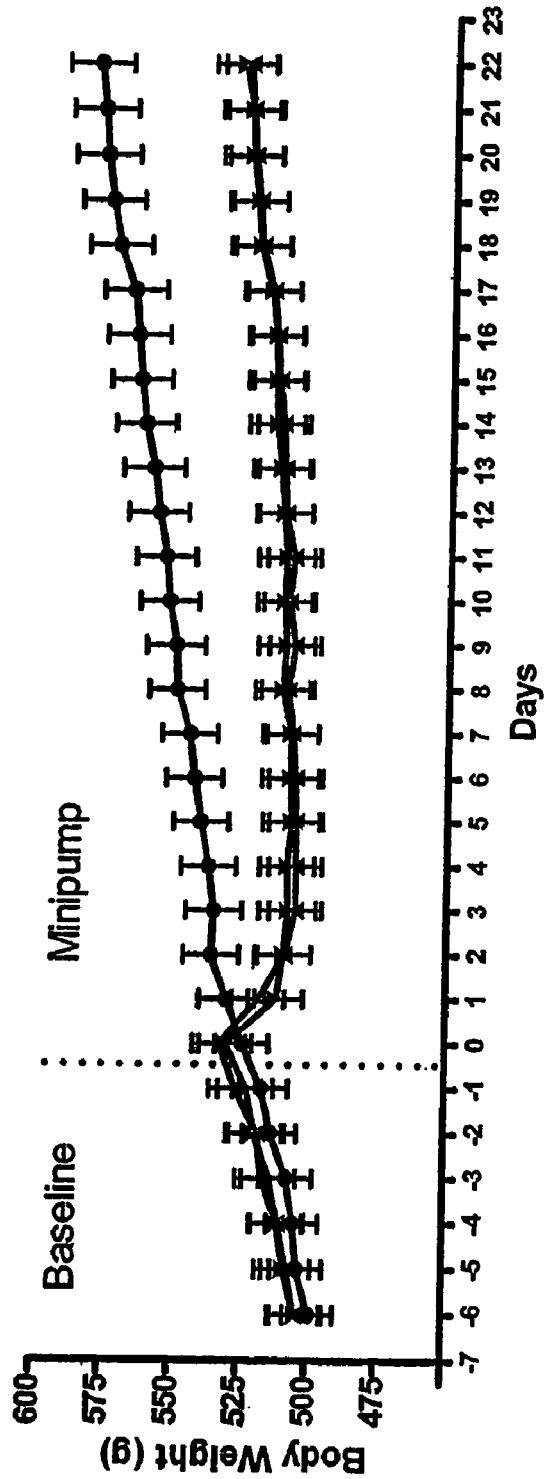
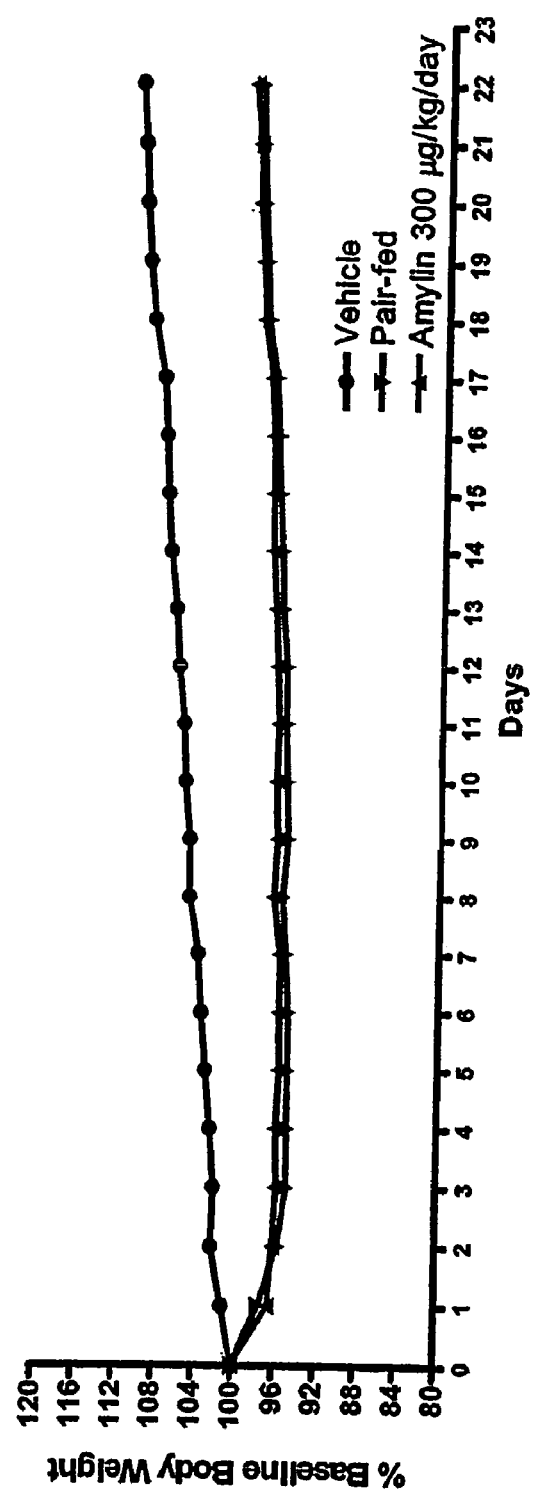
Fig. 8A
Fig. 8B

* $P < 0.05$, compared to vehicle.

* $P < 0.05$, compared to vehicle.

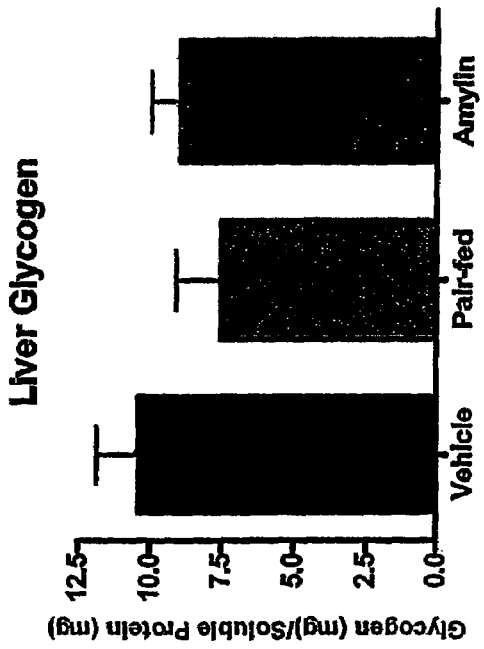
Fig. 11B Liver Glycogen
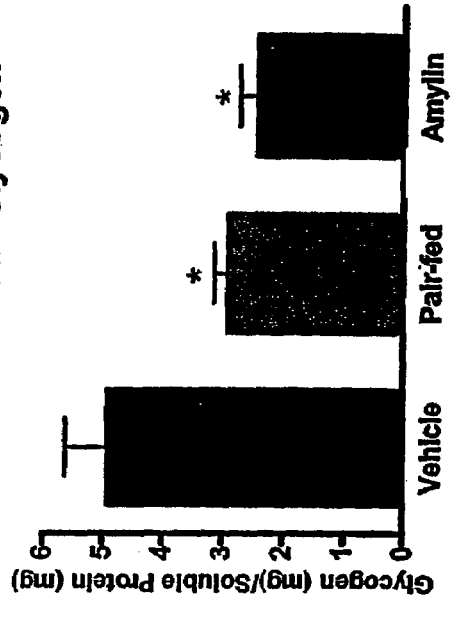
Fig. 11D Gastrocnemius Glycogen
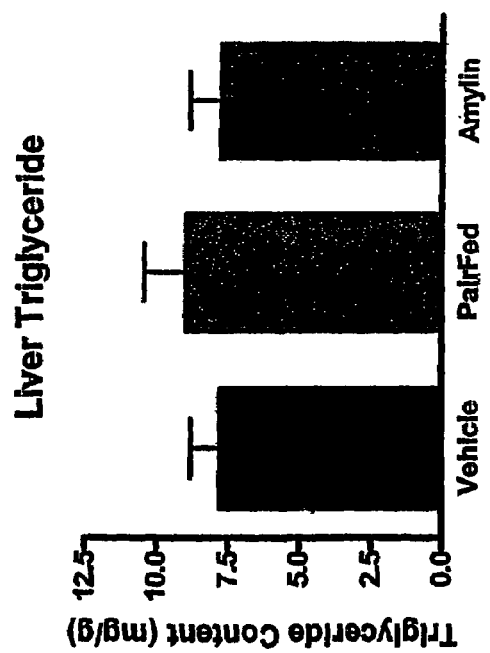
Fig. 11A Liver Triglyceride
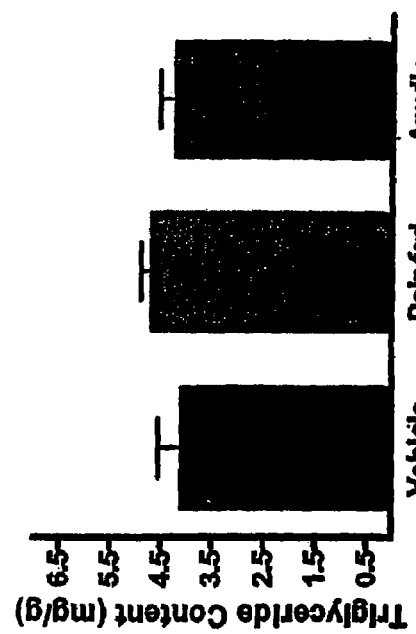
Fig. 11C Gastrocnemius Triglyceride
\* $P < 0.05$, compared to vehicle.

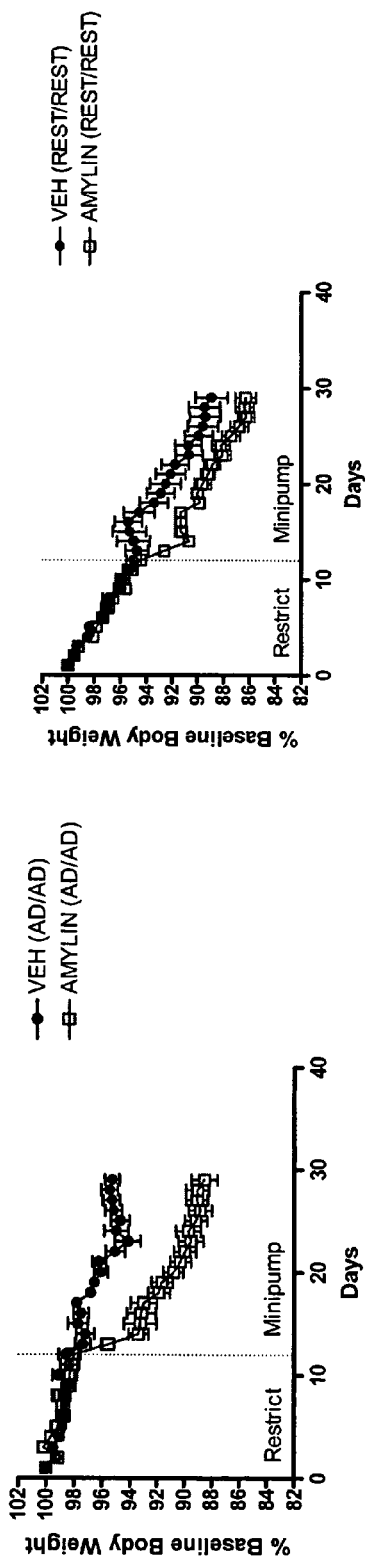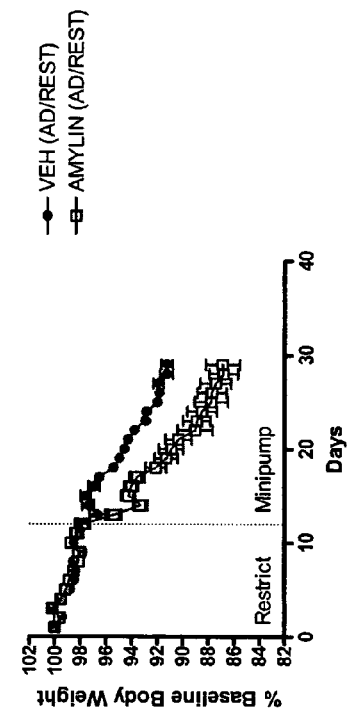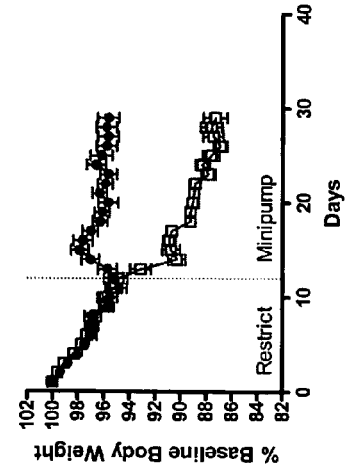
Fig. 13 A
Fig. 13 B
Fig. 13 C
Fig 13 D

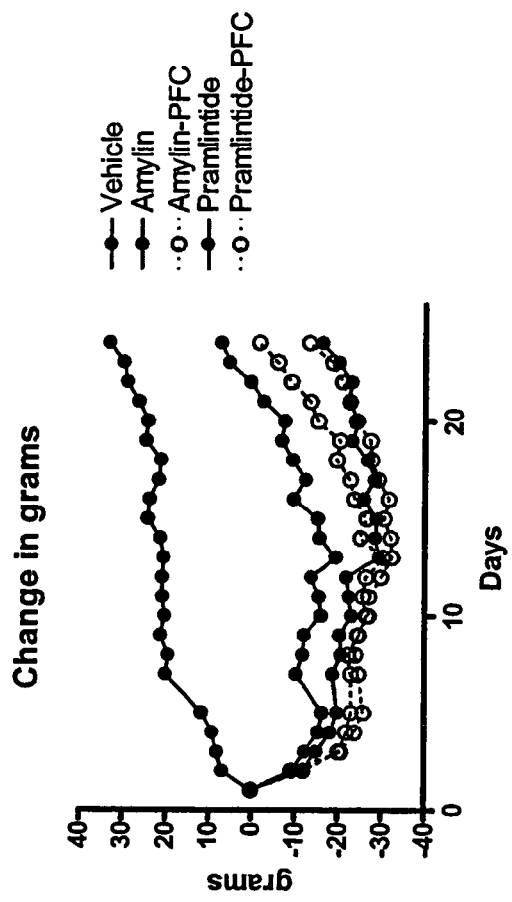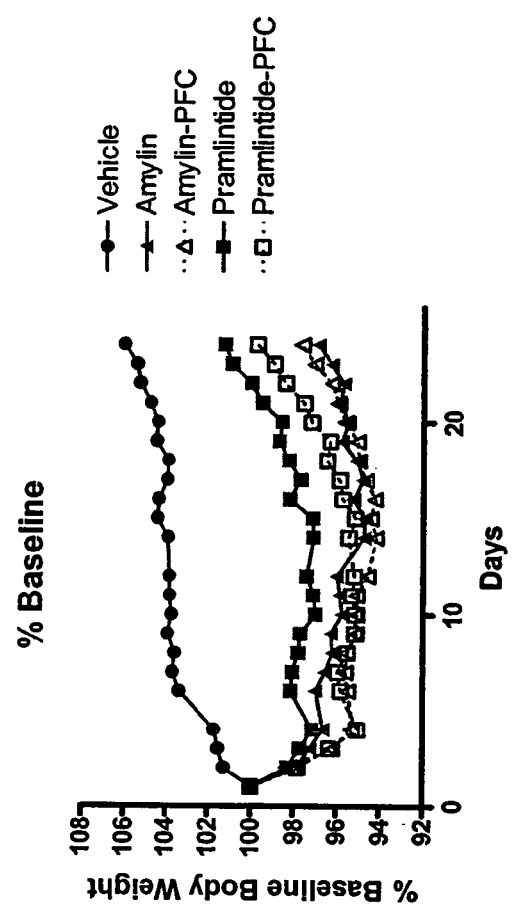
Fig. 14C
Fig. 14D

METHODS FOR AFFECTING BODY COMPOSITION

CROSS REFERENCE TO RELATED APPLICATIONS

This application claims the benefit of priority to provisional U.S. Patent Application Ser. No. 60/550,447, filed Mar. 4, 2004, and incorporates by reference its contents in its entirety.

FIELD OF THE INVENTION

The present invention relates to the fields of medicine, health and nutrition.

BACKGROUND OF THE INVENTION

It is estimated that about 64% of Americans are overweight or obese (roughly about 97 million adults) and it is generally believed that these numbers are increasing. Being obese or overweight may substantially increase the risk of morbidity from hypertension; dyslipidemia; type 2 diabetes; coronary heart disease; stroke; gallbladder disease; osteoarthritis; sleep apnea and respiratory problems; and endometrial, breast, prostate, and colon cancers. Higher body weights are also associated with increases in all-cause mortality. Furthermore, being obese or overweight may cause a person to have negative self-image about him or her self.

In humans, patients who are overweight or obese are considered those with a Body Mass Index (BMI) of equal or greater than 25. BMI is a common measure expressing the relationship (or ratio) of weight-to-height. It is a mathematical formula in which a person's body weight in kilograms is divided by the square of his or her height in meters (i.e., $wt/(ht)^2$). Individuals with a BMI of 25 to 29.9 are considered overweight, while individuals with a BMI of 30 or more are considered obese.

According to the NIH Clinical Guidelines on the Identification, Evaluation, and Treatment of Overweight and Obesity in Adults, all adults (aged 18 years or older) who have a BMI of 25 or more are considered at risk for premature death and disability as a consequence of overweight and obesity. These health risks increase even more as the severity of an individual's obesity increases.

For these reasons, there is an enormous interest in treating obesity. Existing therapies include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery, such as gastric bypass. Jung and Chong, *Clinical Endocrinology*, 35:11-20 (1991); Bray, *Am. J. Clin. Nutr.*, 55:538S-544S (1992).

In general, however, while loss of fat is desired, loss of lean body mass (protein) is not. Lean body mass is highly active metabolically and physiologically and the size is generally genetically defined and maintained. Lean body mass contains all the body protein. There is no real protein store as every protein molecule has a role in maintaining homeostasis. It is believed that loss of body protein is deleterious to the health of an individual. The majority of the protein in the lean body mass is in the skeletal muscle mass. Lean body mass is 50-60% muscle mass by weight, the rest is bone and tendon. Protein makes up the critical cell structure in muscle, viscera, red cells and connective tissue. Enzymes, which direct metabolism, and antibodies, which maintain immune function, are also proteins. Thus, it is desirable to prevent or minimize loss of lean body mass even while reducing body fat.

Caloric restriction, regardless of its form, can cause catabolism of body protein and produce negative nitrogen balance. Protein-supplemented diets, therefore, have gained popularity as a means of lessening nitrogen loss during caloric restriction. Protein-sparing modified fasting has been reported to be effective in weight reduction in adolescents. Lee et al. *Clin. Pediatr.*, 31:234-236 (April 1992). However, these diets may produce only modest nitrogen sparing. A need exists for effective ways of promoting fat loss yet preserving lean body mass or minimizing its loss.

What are described herein are novel methods for modifying body composition.

SUMMARY OF THE INVENTION

In one general aspect, methods of the invention include the use of an amylin or an amylin agonist to modify body composition, for example, reducing body fat, but not lean body mass. The change in body composition can be by weight (e.g., loss or gain by grams) or by percent body fat and percent lean body mass or protein.

Methods for treating obesity using amylin and amylin agonists have been described in U.S. patent application Ser. No. 09/445,517, filed Jun. 5, 1998, and U.S. patent application Ser. No. 08/870,762, filed Jun. 6, 1997, the entire contents of which have been incorporated herein. However, it has surprisingly been discovered that amylin and amylin agonists may have a metabolic effect and may also be used to affect body composition, leading to the desirable loss of body fat, yet preserving lean body mass or minimizing its loss. Moreover, amylin did not induce tolerance/resistance in a subject when administered by osmotic pump, unlike sibutramine.

In certain embodiments, methods of the invention include reducing body fat or preventing body fat gain. Other embodiments include controlling body weight and/or sculpting a body's appearance. The subjects to whom these methods may be of interest are those individuals who are overweight or obese. However, subjects with lean body composition, for example, body builders and other athletes, may benefit from the invention as well. It may be desirable for them to reduce or maintain their body weight, e.g., to stay in a certain weight class range, yet preserve or increase their lean body mass for greater strength, stamina, endurance and/or a more muscular appearance. Such methods may also be used on any animal for which a greater lean body mass to fat ratio is desired. Examples of such use include, but are not limited to, creating a superior show dog or creating a superior racehorse.

In certain embodiments of the invention, administration of an amylin or an amylin agonist is done peripherally and not centrally, i.e., not through the central nervous system. In a preferred embodiment, a therapeutically or prophylactically effective amount of an amylin or an amylin agonist is administered in a single dose, multiple doses, or continuous administration.

It is also contemplated that methods of the invention include amylin agonists described in more detail in U.S. patent application Ser. No. 60/543,275, filed Feb. 11, 2004, the contents of which are incorporated by reference in its entirety. These amylin agonists will generally retain, at least in part, a biological activity similar to that of native human amylin, i.e., the agonist will generally have amylin-like activity. For example, they may exhibit amylin activity in the treatment or prevention of metabolic conditions and disorders.

It is further contemplated that methods of the invention can be used in combination with other forms of nutritional regimens and weight loss programs, such as those already described above, for example, those that include life-style changes that include monitoring food intake (quantity and quality) and exercising, as well as including diet drugs and surgery.

In yet another general aspect, methods of the invention can include the use of amylin and amylin agonists to reduce the fat content in animals for consumption. In other words, methods of the invention can include producing a leaner meat source. Thus, the present invention can be used with livestock including, but not limited to, chicken, cows, pigs, and sheep.

The details of one or more embodiments of the invention are set forth in the accompanying drawings and the description below. Other features, objects, and advantages of the invention will be apparent from the description and drawings, and from the claims. All references cited herein are incorporated by reference.

BRIEF DESCRIPTION OF THE DRAWINGS

FIGS. 6A and 6B depict the effect of amylin on weight in lean rats.

FIGS. 8A and 8B depict the effect of amylin on weight in DIO Levin rats.

FIGS. 11A-11D depict the tissue biochemistry of DIO Levin rats chronically administered amylin.

FIGS. 14A-14H depict the effect of amylin and pramlintide on food intake, body weight and body composition in rats.

DESCRIPTION OF THE INVENTION

Figure 1A:
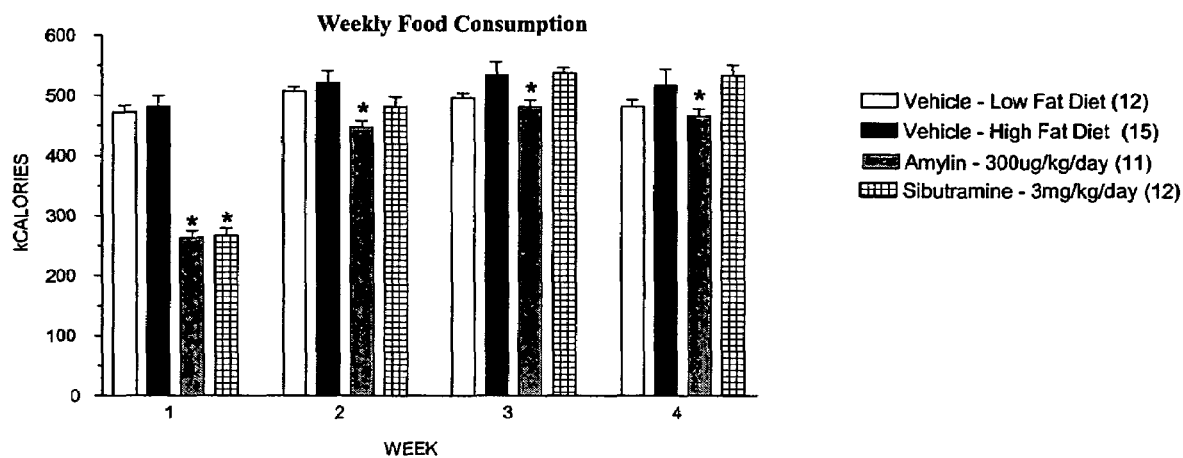
FIGS. 1A and 1B depict the effects of chronic administration of amylin or sibutramine on food consumption and body weight, respectively, in DIO rats.
Figure 1B:
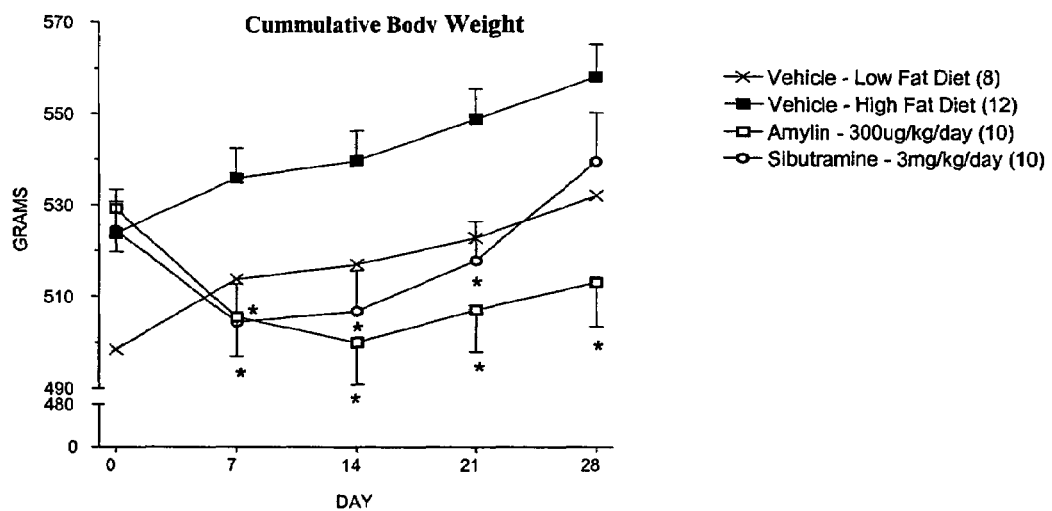

It has now been discovered that amylin and amylin agonist, which also include amylin agonist analogs and derivatives, may have metabolic effects on the body and may be used to preferentially reduce body fat and spare, or increase, lean body mass.

The present invention is directed to affecting body composition by reducing body weight, maintaining body weight, or reducing body weight gain, while selectively reducing body fat or preventing body fat gain and maintaining or increasing lean body mass. In certain situations, however, it may be desirable to increase body weight, for example, through selective nutrient intake (e.g., increasing the caloric or fat content), while reducing or maintaining percent body fat, e.g., body building.

The methods of the invention contemplate the administration of an effective amount of an amylin or an amylin agonist to a body to affect the desired results as described in the claimed methods.

The administered amylin or amylin agonist may be in the form of a peptide, a prodrug, or as pharmaceutical salts thereof. The term "prodrug" refers to a compound that is a drug precursor that, following administration, releases the drug in vivo via some chemical or physiological process, for example, proteolytic cleavage, or upon reaching an environment of a certain pH.

Methods of the invention can be used on any individual in need of such methods or individuals for whom practice of the methods is desired. These individuals may be any mammal including, but not limited to, humans, dogs, horses, cows, pigs, chicken and other commercially valuable or companion animals.

Amylin and Amylin Agonists

Human amylin is a 37 amino acid peptide hormone that is co-secreted with insulin from pancreatic β-cells in response to nutrient stimuli. Human amylin has the following amino acid sequence:

Lys-Cys-Asn-Thr-Ala-Thr-Cys-Ala-Thr-Gln Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1).

"Amylin" is meant to include polypeptides obtained or derived from any species. Thus, the term "amylin" includes the human full-length amino acid peptide, and species variations of amylin, including e.g., murine, hamster, chicken, bovine, rat, and dog amylin.

Amylin agonists contemplated in the use of the invention are those compounds having at least one amylin-like activity. "Amylin-like activity" or "amylin activity," as used herein, can be the ability to reduce food intake, body weight, or alter body composition. "Amylin-like activity" or "amylin activity" can also be the ability to bind to, or otherwise directly or indirectly interact with, an amylin receptor or other receptor(s) with which amylin may interact to elicit a biological response, in particular altering body composition. An amylin agonist may be a peptide or a non-peptide compound and includes amylin agonist analogs. Exemplary amylin receptors and their use in methods for screening and assaying for amylin agonists are described in U.S. Pat. No. 5,264,372, issued Nov. 23, 1993, incorporated herein by reference. "Amylin-like activity" or "amylin activity" may also include any one or more of those amylin activities described in U.S. patent application Ser. No. 09/445,517, filed Jun. 5, 1998, previously incorporated by reference. Assays for measuring amylin activity are known in the art, for example the receptor binding assays, soleus muscle assay, and gastric emptying assay, which are described in the above patent application, as well as food intake assays described in U.S. Provisional Application No. 60/543,275, filed on Feb. 11, 2004, the content of which is incorporated by reference in its entirety.

Amylin agonists useful in the invention may have an amylin activity greater than or less than native amylin for a particular activity. Thus, for example, amylin agonists may have 3, 5, 10, 50, 100, 500, 1000 times or more activity than native amylin. Furthermore, while it is desirable to use an amylin agonist having similar or greater activity than native amylin, one of ordinary skill in the art would understand that agonists having less activity than native amylin would also be useful in the present invention. Such agonists, for example, may have anywhere from 2, 5, 10, 15, or 20 times less activity than native amylin. Examples of such agonists, more particularly known as amylin agonists analogs (analogs and derivatives of amylin), are described in U.S. Pat. Nos. 5,686,411, 6,114, 304, 6,410,511, and 6,610,824, as well as patent application Ser. No. 454,533 (filed Dec. 6, 1999), the contents of which are incorporated by reference in their entirety. Amylin agonist analogs also include those compounds described in U.S. Provisional Application No. 60/543,275, filed on Feb. 11, 2004, previously incorporated by reference. Amylin agonist analogs useful in the invention may also include fragments of amylin such as those described in EP 289287, the contents of which are herein incorporated by reference.

Amylin agonist analogs useful in the methods of this application include amylin agonist analogs having the following amino acid sequence:

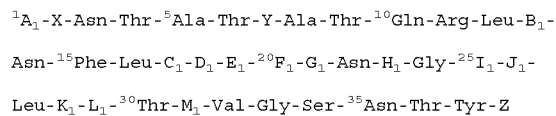

$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}I_1$-$J_1$-Leu-$K_1$-$L_1$-$^{30}$Thr-$M_1$-Val-Gly-Ser-$^{35}$Asn-Thr-Tyr-Z wherein $A_1$ is hydrogen Lys, Ser, Ala, des-α-amino Lys, or acetylated Lys; $B_1$ is Ala, Ser or Thr; $C_1$ is Val, Leu or Ile; $D_1$ is His or Arg; $E_1$ is Ser or Thr; $F_1$ is Ser, Thr, Gln or Asn; $G_1$ is Asn, Gln or His; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp or Gln; X and Y are independently selected residues having side chains which are chemically bonded to each other to form an intramolecular linkage; and Z is hydroxy, amino, alkylamino, dialkylamino, cycloalkylamino, arylamino, aralkylamino, alkyloxy, aryloxy or aralkyloxy; provided that (a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1^{Ile, K}{}_{is\ Ser, L1}$ is Ser, and $M_1$ is Asn; (b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (c) when $A_1$ is Lys, $B_1$ is Ala., $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (d) when $A_1$ is Lys, $B_1$ is Ala. $C_1$ is Val, $D_1$ is Arg, $E_1$ is Ser, $F_1$ is Ser, $G_1$ is Asn, $H_1$ is Lea, $I_1$ is Pro, $J_1$ is Val, $K_1$ is Pro, $L_1$ is Pro, and $M_1$ is Asn; (e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn; or (f) when $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ Leu, $L_1$ is Pro and $M_1$ is Asp; then one or more of any of $A_1$ to $M_1$ is not an L-amino acid and Z is not amino [SEQ ID NO: 29].

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

As used herein, the following terms have the following meanings unless expressly stated to the contrary:

The term "alky" refers to both straight- and branched-chain alkyl groups. The term "lower alkyl" refers to both straight- and branched-chain alkyl groups having a total of from 1 to 6 carbon atoms and includes primary, secondary, and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like.

The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl.

The term "cycloalkyl" refers to cyclic alkyl groups of 5 to 8 carbon atoms.

Biologically active derivatives of the above agonist analogs are also included within the scope of amylin agonist analogs useful in the present invention in which the stereochemistry of individual amino acids may be inverted from (L)/S to (D)/R at one or more specific sites. Also included within the scope of amylin agonist analogs useful in the present invention are the agonist analogs modified by glycosylation of Asn, Ser and/or Thr residues.

Biologically active agonist analogs of amylin which contain less peptide character are also included in the scope of amylin agonist analogs useful in the present invention. Such peptide mimetics may include, for example, one or more of the following substitutions for —CO—NH— amide bonds: depsipeptides (—CO—O—), iminomethylenes (—CH$^2$—NH—), trans-alkenes (—CH≈CH—), β-enaminonitriles (—C(=CH—CN)—NH—), thioamides (—CS—NH—), thiomethylenes (—S—CH$_2$— or —CH$_2$—S—), methylenes, and retro-amides (—NH—CO—).

The above-described amylin agonist analogs form salts with various inorganic and organic acids and bases. Such salts include salts prepared with organic and inorganic acids, for example, HCl, HBr, H2SO$_4$, H$_3$PO$_4$, trifluoroacetic acid, acetic acid, formic acid, methanesulfonic acid, toluenesulfonic acid, maleic acid, fumaric acid, and camphorsulfonic acid. Salts prepared with bases include, for example, ammonium salts, alkali metal salts (such as sodium and potassium salts), and alkali earth salts (such as calcium and magnesium salts). Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin. The above-described amylin agonist analogs include various stereoisomers. In the preferred amylin agonist analogs, the chiral centers on the peptide backbone are all S.

The nomenclature of various amylin agonist analogue compounds useful in the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "$^{18}$Arg$^{25,28}$Pro-h-amylin" [SEQ ID NO:32] refers to a peptide based on the sequence of "h-amylin" or "human-amylin" having the following substitutions: Arg replacing His at residue 18, Pro replacing Ala at residue 25 and Pro replacing Ser at residue 28. The term "des-$^1$Lys-h-amylin" [SEQ ID NO:33] refers to a peptide based on the sequence of human amylin, with the first, or N-terminal, amino acid deleted.

The agonist analogs of amylin of this invention are useful in view of their pharmacological properties. Activity as amylin agonist agents can be indicated by activity in the receptor binding assay and the soleus muscle assay described below. Amylin agonist activity of compounds may also be assessed by the ability to modify body composition as described herein.

Preferred amylin agonist analogue compounds include des-$^1$Lys-h-amylin [SEQ ID NO:33], $^{28}$Pro-h-amylin [SEQ ID NO:34], $^{25,28,29}$Pro-h-amylin [SEQ ID NO:30], $^{18}$Arg$^{25,28}$Pro-h-amylin [SEQ ID NO:32], and des-$^1$Lys$^{18}$Arg$^{25,28}$Pro-h-amylin [SEQ ID NO:35]. In addition to having activities characteristic of amylin, certain preferred compounds have also been found to possess more desirable solubility and stability characteristics when compared to human amylin. These preferred compounds include $^{25}$Pro$^{26}$Val$^{28,29}$Pro-h-amylin [SEQ ID NO:36], $^{25,28,29}$Pro-h-amylin [SEQ ID NO:30] (also referred to herein as "AC-0137"), and $^{18}$Arg$^{25,28}$Pro-h-amylin [SEQ ID NO:32].

The method of the present invention can employ an amylin agonist, including amylin or an amylin agonist analogue, for example, amylin receptor agonist analogs such as $^{18}$Arg$^{25,28}$Pro-h-amylin [SEQ ID NO:32], des-$^1$Lys$^{18}$Arg$^{25,28}$Pro-h-amylin [SEQ ID NO:35], $^{18}$Arg$^{25,28,29}$Pro-h-amylin [SEQ ID NO: 37], des-$^1$Lys$^{18}$Arg$^{25,28,29}$Pro-h-amylin [SEQ ID NO:38], $^{25,28,29}$Pro-h-amylin [SEQ ID NO:30], des-$^1$Lys$^{25,28,29}$Pro-h-amylin [SEQ ID NO:39], and $^{25}$Pro$^{26}$Val$^{25,28}$Pro-h-amylin [SEQ ID NO:36]. Examples of other suitable amylin agonist analogs include:

$^{23}$Leu$^{25}$Pro$^{26}$Val$^{28,29}$Pro-h-amylin; [SEQ ID NO:40]

$^{23}$Leu$^{25}$Pro$^{26}$Val$^{28}$Pro-h-amylin; [SEQ ID NO:41]

des-$^1$Lys$^{23}$Leu$^{25}$Pro$^{26}$Val$^{28}$Pro-h-amylin; [SEQ ID NO:42]

$^{18}$Arg$^{23}$Leu$^{25}$Pro$^{26}$Val$^{28}$Pro-h-amylin; [SEQ ID NO:43]

$^{18}$Arg$^{23}$Leu$^{25,28,29}$Pro-h-amylin; [SEQ ID NO:44]

$^{18}$Arg$^{23}$Leu$^{25,28}$Pro-h-amylin; [SEQ ID NO:45]

$^{17}$Ile$^{23}$Leu$^{25,28,29}$Pro-h-amylin; [SEQ ID NO:46]

$^{17}$Ile$^{25,28,29}$Pro-h-amylin; [SEQ ID NO:47]

des-$^1$Lys$^{17}$Ile$^{23}$Leu$^{25,28,29}$Pro-h-amylin; [SEQ ID NO:48]

$^{17}$Ile$^{18}$Arg$^{23}$Leu-h-amylin; [SEQ ID NO:49]

$^{17}$Ile$^{18}$Arg$^{23}$Leu$^{26}$Val$^{29}$Pro-h-amylin; [SEQ ID NO:50]

$^{17}$Ile$^{18}$Arg$^{23}$Leu$^{25}$Pro$^{26}$Val$^{28,29}$Pro-h-amylin; [SEQ ID NO:51]

[SEQ ID NO:52]
$^{13}$Thr-His$^{23}$Leu$^{26}$Ala$^{28}$Leu$^{29}$Pro$^{31}$Asp-h-amylin;

[SEQ ID NO:53]
$^{13}$Thr$^{21}$His$^{23}$Leu$^{26}$Ala$^{29}$Pro$^{31}$Asp-h-amylin;

[SEQ ID NO:54]
des-$^1$Lys$^{13}$Thr$^{21}$His$^{23}$Leu$^{26}$Ala$^{28}$Pro$^{31}$Asp-h-amylin;

[SEQ ID NO:55]
$^{13}$Thr$^{18}$Arg$^{21}$His$^{23}$Leu$^{26}$Ala$^{29}$Pro$^{31}$Asp-h-amylin;

[SEQ ID NO:56]
$^{13}$Thr$^{18}$Arg$^{21}$His$^{23}$Leu$^{28,29}$Pro$^{31}$Asp-h-amylin; and,

[SEQ ID NO:57]
$^{13}$Thr$^{18}$Arg$^{21}$His$^{23}$Leu$^{25}$Pro$^{26}$Ala$^{28,29}$Pro$^{31}$Asp-h-amylin.

Still further amylin agonists including amylin agonist analogs are disclosed in WPI Acc. No. 93-182488/22, "New Amylin Agonist Peptides Used for Treatment and Prevention of Hypoglycemia and Diabetes Mellitus," the disclosure of which has been incorporated by reference.

$^{25,28,29}$Pro-h-amylin [SEQ ID NO:30] which is also referred to as "pramlintide," is a most preferred agonist of human amylin. $^{25,28,29}$Pro-h-amylin will be referred to as "pramlintide" hereafter. Pramlintide is substantially different from and better than human amylin, retaining the desired biological properties of human amylin with superior attributes, including superior pharmaceutical properties (L. S. L. Gaeta and T. J. Rink, *Medicinal Chemistry Research*, 1994).

The activity of amylin agonists may be evaluated using certain biological assays described herein. The receptor binding assay can identify both candidate amylin agonists and antagonists and can be used to evaluate binding, while the soleus muscle assay distinguishes between amylin agonists and antagonists. Effects of amylins or amylin agonists on metabolism can be identified, evaluated, or screened for using the methods described in the Examples below, or other art-known or equivalent methods for determining metabolism.

Preferably, agonist compounds exhibit activity in the receptor binding assay on the order of less than about 1 to 5 nM, preferably less than about 1 nM and more preferably less than about 50 pM. In the soleus muscle assay these compounds preferably show $EC_{50}$ values on the order of less than about 1 to 10 micromolar.

The receptor binding assay is described in U.S. patent application Ser. No. 670,231, filed on Mar. 15, 1991, and published on Oct. 1, 1992 as International Application Number PCT/US92/02125, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson, P. and Rodbard, D.,*Anal. Biochem.* 107:220-239 (1980).

Assays of biological activity of amylin agonists, including amylin agonist analogue preparations in the soleus muscle are performed using previously described methods (Leighton, B. and Cooper, G. J. S., *Nature*, 335:632-635 (1988); Cooper, G. J. S., et al., *Proc. Natl. Acad. Sci. USA* 85:7763-7766 (1988)). In summary, amylin agonist activity is assessed by measuring the inhibition of insulin-stimulated glycogen synthesis in soleus muscle. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as agonists in this assay is determined by measuring $EC_{50}$ values. Standard errors are determined by fitting of sigmoidal dose response curves using a four parameter logistic equation (De Lean, A., Munson, P. J., Guardabasso, V. and Rodbard, D. (1988) *ALLFIT*, Version 2.7, National Institute of Child Health and Human Development, N.I.H. Bethesda, Md., 1 diskette). A number of amylin agonists have been characterized using these biological assays. The compounds $^{18}\text{Arg}^{25,28}\text{Pro-h-amylin}$ [SEQ ID NO:32], $\text{des}^{1}\text{Lys}^{18}\text{Arg}^{25,28}\text{Pro-h-amylin}$ [SEQ ID NO:35], $^{18}\text{Arg}^{25,28,29}\text{Pro-h-amylin}$ [SEQ ID NO:37], $\text{des}^{1}\text{Lys}^{18}\text{Arg}^{25,28,29}\text{Pro-h-amylin}$ [SEQ ID NO:38], $^{25,28,29}\text{Pro-h-amylin}$ [SEQ ID NO:30], $\text{des}^{1}\text{Lys}^{25,28,29}\text{Pro-h-amylin}$ [SEQ ID NO:39], and $^{25}\text{Pro}^{26}\text{Val}^{25,28}\text{Pro-h-amylin}$ [SEQ ID NO:36] were all found to compete with amylin in the receptor binding assay. These compounds have negligible antagonist activity as measured by the soleus muscle assay and were shown to act as amylin agonists. Similar results were obtained with other agonist compounds listed above.

Compounds such as those described above are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer were purchased from Applied Biosystems Inc. (Foster City, Calif.), unless otherwise indicated. The side-chain protected amino acids used and purchased from Applied Biosystem, Inc. included the following: Boc-Arg(ts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys (Boc), Boc-Glu(Bzl), Fmoc-Glu(t-Bu), Fmoc-His(Trt), Fmoc-Asn(Trt), and Fmoc-Gln(Trt). Boc-His(BOM) was purchased from Applied Biosystems, Inc. or Bachem Inc. (Torrance, Calif.). Anisole, methylsulfide, phenol, ethanedithiol, and thioanisole were obtained from Aldrich Chemical Company (Milwaukee, Wis.). Air Products and Chemicals (Allentown, Pa.) supplied HF. Ethyl ether, acetic acid and methanol were purchased from Fisher Scientific (Pittsburgh, Pa.).

Solid phase peptide synthesis was carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins were cleaved with HF (−50° C. to 0° C., 1 hour). The peptide was extracted from the resin with alternating water and acetic acid, and the filtrates were lyophilized. The Fmoc-peptide resins were cleaved according to standard methods (*Introduction to Cleavage Techniques*, Applied Biosystems, Inc., 1990, pp. 6-12). Some peptides were also assembled using an Advanced. Chem. Tech Synthesizer (Model MPS 350, Louisville, Ky.). Peptides were purified by RP-HPLC (preparative and analytical) using a Waters Delta Prep 3000 system. A C4, C8 or C 18 preparative column (10µ, 2.2×25 cm; Vydac, Hesperia, Calif.) was used to isolate peptides, and purity was determined using a C4, C8 or C18 analytical column (5µ, 0.46×25 cm; Vydac). Solvents (A=0.1% TFA/water and B=0.1% TFA/$CH_3CN$) were delivered to the analytical column at a flowrate of 1.0 ml/min and to the preparative column at 15 ml/min. Amino acid analyses were performed on the Waters Pico Tag system and processed using the Maxima program. The peptides were hydrolyzed by vapor-phase acid hydrolysis (115° C., 20-24 h). Hydrolysates were derivatized and analyzed by standard methods (Cohen, S. A., Meys, M., and Tarrin, T. L. (1989), *The Pico Tag Method: A Manual of Advanced Techniques for Amino Acid Analysis*, pp. 11-52, Millipore Corporation, Milford, Mass.). Fast atom bombardment analysis was carried out by M-Scan, Incorporated (West Chester, Pa.). Mass calibration was performed using cesium iodide or cesium iodide/glycerol. Plasma desorption ionization analysis using time of flight detection was carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989).

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Amylin agonists include polypeptides described in U.S. Patent Application No. 60/543,275, previously incorporated by reference, as well as their analogs and derivatives. These polypeptides include:

```
                                                    (SEQ ID NO:2)
c(KCNTATCATQRLANFLVRSSNNLTNVGSNTY-NH2), (SEQ ID NO:3)
c(KCNTATCATQRLANELVRLQTYPRTNVGSNTY-NH2), (SEQ ID NO:4)
```

-continued c(CSNLSTCVLGRLSQELHRLQTYPRTNTGSNTY-NH2), (SEQ ID NO:5)
c(KCNTATCVLGRLSQELHRLQTYPRTNTGSNTY)-NH2), (SEQ ID NO:6)
Isocap-STAVL-(Aib)-K(formyl)-LSQEL-(Aib)-K(formyl)-LQTYPRTNTGSGTP-NH2, (SEQ ID NO:7)
c(KCNTATCATQRLANALVHSSNNFGAILPSTNVGSNTY-NH2), (SEQ ID NO:8)
c(KCNTATCATARLAAFLARSSGY-NH2), (SEQ ID NO:9)
c(KCNTATCATQRLANFLVHSGNNFGAILSSTNVGSNTY-NH2), (SEQ ID NO:10)
c(CNTATCATARLAAFLARS-NH2), (SEQ ID NO:11)
c(KCNTATCVLGKLSQELHRLQTYPRTNTGSNTY-NH2), (SEQ ID NO:12)
c(KCNTATCVLGRLSQELHRLQTLPRTNTGSNTY-NH2), (SEQ ID NO:13)
c(KCNTATCVLGRLSQELHRLQTYPPTNTGSNTY-NH2), (SEQ ID NO:14)
c(KCNTATCVLGRLSQELHRLQTYPRTNVGSNTY-NH2), (SEQ ID NO:15)
c(KCNTATCVLGRLSQELHRLQTLPPTNVGSNTY-NH2), (SEQ ID NO:16),
c(KCNTATCVLGRLANFLHRLQTYPRTNTGSNTY-NH2), (SEQ ID NO:17)
c(ACNTATCVLGRLSQELHRLQTYPRTNTGSNTY-NH2), (SEQ ID NO:18)
c(KCATATCVLGRLSQELHRLQTYPRTNTGSNTY-NH2), (SEQ ID NO:19)
c(KCNAATCVLGRLSQELHRLQTYPRTNTGSNTY-NH2), (SEQ ID NO:20)
c(KCNTAACVLGRLSQELHRLQTYPRTNTGSNTY-NH2), (SEQ ID NO:21)
c(CANLSTCVLGRLSQELHRLQTYPRTNTGSNTY-NH2), (SEQ ID NO:22)
Isocap-STAVLGRLSQELHRLQTYPRTNTGSNTY-NH2, (SEQ ID NO:23)
c(CSNASTCVLGRLSQELHRLQTYPRTNTGSNTY-NH2, (SEQ ID NO:24)
c(CSNLATCVLGRLSQELHRLQTYPRTNTGSNTY-NH2), (SEQ ID NO:25)
c(CSNLSACVLGRLSQELHRLQTYPRTNTGSNTY-NH2), (SEQ ID NO:26)
c(KCNTATCVLGRLSQELHKLQTYPRTNTGSNTY-NH2), (SEQ ID NO:27)
c(KCNTATCVLGRLSQELHRLQTYPRTNTGSGTP-NH2), and (SEQ ID NO:28)
c(KCNTATCATQRLSQELHRLQTYPRTNTGSGTP-NH2).

Amylin agonist analogs may also be compounds having at least 60, 65, 70, 75, 80, 85, 90, 95, 98, or 99% amino acid sequence identity to any of SEQ ID NOs:1 through 28, as well as fragments thereof, and have an amylin activity.

Amylin agonist analogs may further include analogs and derivatives of amylin having insertions, extensions, deletions and/or substitutions in at least one or more amino acid positions of SEQ ID NOs:1 through 28, and having amylin activity. The number of amino acid insertions, extensions, deletions, or substitutions may be at least 5, 10, 15, 20, 25, or 30. Insertions, extensions, or substitutions may be with other natural amino acids, synthetic amino acids, peptidomimetics, or other chemical compounds. The analog polypeptides of the invention may be derivatized by chemical alterations such as amidation, glycosylation, acylation, sulfation, phosphorylation, acetylation, and cyclization. Such chemical alterations may be obtained through chemical or biochemical methodologies, as well as through in-vivo processes, or any combination thereof. Derivatives of the analog polypeptides of the invention may also include conjugation to one or more polymers or small molecule substituents. One type of polymer conjugation is linkage or attachment of polyethylene glycol ("PEG") polymers, polyamino acids (e.g., poly-his, poly-arg, poly-lys, etc.) and/or fatty acid chains of various lengths to the N— or C-terminus or amino acid residue side chains of a polypeptide analog. Small molecule substituents include short alkyls and constrained alkyls (e.g., branched, cyclic, fused, adamantyl), and aromatic groups.

Amylin agonists useful in the invention may also include calcitonins, such as teleost calcitonins, and their analogs and derivatives, as well as calcitonin-gene-related peptides (CGRP) and their analogs and derivatives.

Methods of the invention contemplate the use of one or more of the compounds known as amylin, amylin agonist analog, or amylin agonist.

Dosage/Formulation

Amylin and amylin agonist (herein referred to as the "amylin compounds") may be administered alone or in combination with pharmaceutically acceptable carriers or excipients, in either single or multiple doses. These pharmaceutical compounds may be formulated with pharmaceutically acceptable carriers or diluents as well as any other known adjuvants and excipients in accordance with conventional techniques such as those disclosed in Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988), incorporated by reference.

Exemplary formulations for an amylin or amylin agonist can be found in U.S. Pat. No. 6,410,511 and U.S. patent application Ser. No. 10/159,779, filed May 31, 2002, which are incorporated herein by reference.

In general, the amylin compounds may be formulated into a stable, safe pharmaceutical composition for administration to a patient. Pharmaceutical formulations contemplated for use in the methods of the invention may comprise approximately 0.01 to 1.0% (w/v), preferably 0.05 to 1.0%, of the amylin compound, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In a particular embodiment of the present invention, a pharmaceutical formulation of the present invention may contain a range of concentrations of amylin compounds, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in this embodiment. A sufficient amount of water for injection may be used to obtain the desired concentration of solution.

Additional tonicifying agents such as sodium chloride, as well as other known excipients, may also be present, if desired. It is preferred, however, if such excipients maintain the overall tonicity of the amylin compounds. An excipient may be included in the presently described formulations at various concentrations. For example, an excipient may be included in the concentration range from about 0.02% to about 20% w/w, preferably between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the present peptide formulations, for example, water or an aqueous/organic solvent mixture or suspension.

The stability of a peptide formulation of the present invention is enhanced by maintaining the pH of the formulation in the range of about 3.0 to about 7.0 when in liquid form. Preferably, the pH of the formulation is maintained in the range of about 3.5 to 5.0, or about 3.5 to 6.5, most preferably from about 3.7 to 4.3, or about 3.8 to 4.2. A frequently preferred pH may be about 4.0. While not seeking to be bound by this theory, it is presently understood that where the pH of the pharmaceutical formulation exceeds 5.5, chemical degradation of the peptide may be accelerated such that the shelf life is less than about two years.

The buffer used in the practice of the present invention is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). The most preferred buffer is acetate (preferably at a final formulation concentration of from about 5 to about 30 mM).

A stabilizer may be included in the present formulation but, and importantly, is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient (if this is a desirable property), i.e., the carbohydrate is not metabolized to form unacceptably large concentrations of glucose in the blood.

Preferably, if a stabilizer is included, the amylin compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol. Another useful feature of the lyophilized formulations of the present invention is the maintenance of the tonicity of the lyophilized formulations described herein with the same formulation component that serves to maintain their stability. Mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

An exemplary amylin agonist analog pramlintide, human $^{25,28,29}$Pro-amylin, does not have a tendency to adsorb onto the glass in a glass container when in a liquid form, therefore, a surfactant is not required to further stabilize the pharmaceutical formulation. However, with regard to amylin compounds that do have such a tendency when in liquid form, a surfactant may be used in their formulation. These formulations may then be lyophilized. Surfactants can cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl)dimethylammonio] 1-propanesulfonate), Brij® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations are preferably isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bünder Glas GMBH and Forma Vitrum. The biological and chemical properties of amylin may be stabilized by formulation and lyophilization in a Wheaton Type I-33 borosilicate serum vial to a final concentration of 0.1 mg/ml and 10 mg/ml of amylin in the presence of 5% mannitol, and 0.02% Tween 80.

In order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolactone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 μm and 0.22 μm (1 or 2) which may be connected in series. After filtration, the solution is filled into appropriate vials or containers.

The liquid pharmaceutical formulations of the present invention are intended for parenteral administration. Suitable routes of administration include intramuscular, intravenous, subcutaneous, intradermal, mucosal, intraarticular, intrathecal and the like. These routes include, but are not limited to, oral, nasal, sublingual, pulmonary and buccal routes that may include administration of the amylin compound in liquid, semi-solid or solid form. Administration via some routes require substantially more amylin compound to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The amylin compounds may be provided in dosage unit form. Therapeutically effective amounts of the amylin compound for affecting body composition will vary with many factors including the age and weight of the patient, the patient's physical condition, their use in combination with other treatments, the ultimate goal that is to be achieved, such as overall weight loss and/or maintaining or increasing lean body mass, as well as other factors.

However, typical doses may contain from a lower limit of about 1 μg, 5 μg, 10 g, 50 μg to 100 μg to an upper limit of about 100 μg, 500 μg, 1 mg, 5 mg, 10 mg, 50 mg, or 100 mg of the pharmaceutical compound per day. Also contemplated are other dose ranges such as 0.1 μg to 1 mg of the compound per dose. The doses per day may be delivered in discrete unit doses, provided continuously in a 24 hour period or any portion of that the 24 hours. The number of doses per day may be from 1 to about 4 per day, although it could be more. Continuous delivery can be in the form of a continuous infusion. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c. may be about 6 µg to about 16 mg per day.

EXAMPLE 1

High fat-fed (58% kcal from fat, D12331, Research Diets), male SPRAGUE-DAWLEY® rats were implanted subcutaneously with 28-day osmotic pumps (Durect Corp.) delivering amylin (300 µg/kg/day), sibutramine (3 mg/kg/day), or vehicle (50% dimethyl sulfoxide (DMSO)). Low fat-fed rats (11% kcal from fat, D12329, Research Diets) were also implanted with pumps delivering vehicle. Food intake and body weight measurements were obtained weekly.

Rats were sacrificed by cardiac puncture under anesthesia. Triglyceride levels were measured on a COBAS Mira plasma analyzer (Roche), and leptin and insulin were assayed according to Linco Research rat RIA kits. Body composition was measured by chemical analysis (Covance Laboratories, Madison, Wis.).

Amylin was synthesized by Amylin Pharmaceuticals, Inc. by solid-phase chemistry, purified by HPLC (>98% purity, 84% peptide content), and characterized by amino acid analysis and LC/MS. Sibutramine was extracted from the drug product MERIDIA® using water as a solvent, purified by RP-HPLC (>98% purity), and characterized by NMR and LC/MS.

All data are represented as mean±SEM. Analysis of variance was used to test for group differences.

The rats were fattened for 10 weeks prior to drug treatment. The high fat-fed rats were designated as obesity-prone (top 50% of weight gainers) or obesity-resistant (bottom 50%) based on the amount of weight gained through week 7. No difference between prone and resistant animals was observed for food consumption, body weight, or plasma metabolites in response to drug treatment; therefore, these groups were combined (Table1A, FIGS. 1A, 1B, 3A, 3B, and 3C).

TABLE 1A

| | AMYLIN | | SIBUTRAMINE | |
|---|---|---|---|---|
| Week | Caloric Intake | Body Weight | Caloric Intake | Body Weight |
| 1 | 45%* | 6%* | 45%* | 6%* |
| 2 | 14%* | 7%* | 8%* | 6%* |
| 3 | 10%* | 8%* | −1% | 6%* |
| 4 | 10%* | 8%* | −3% | 3% |

*P < 0.05, significantly different from high fat-fed controls.

Figure 2A:
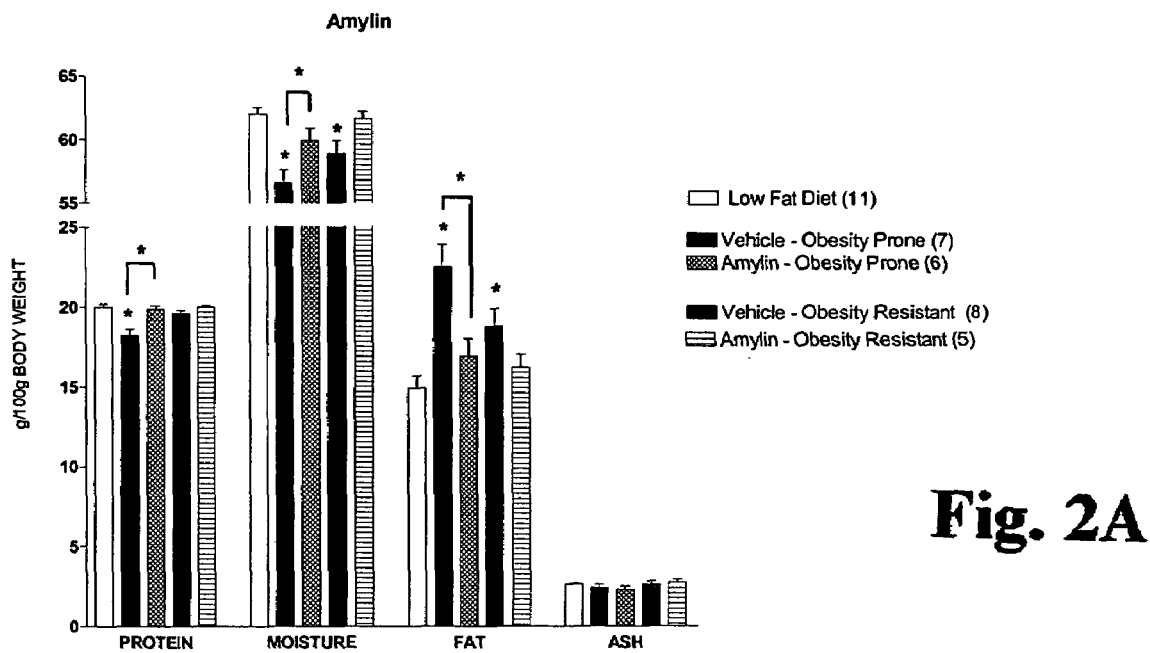
FIGS. 2A and 2B depict the body composition of DIO rats chronically administered with amylin or sibutramine, respectively.
Figure 2B:
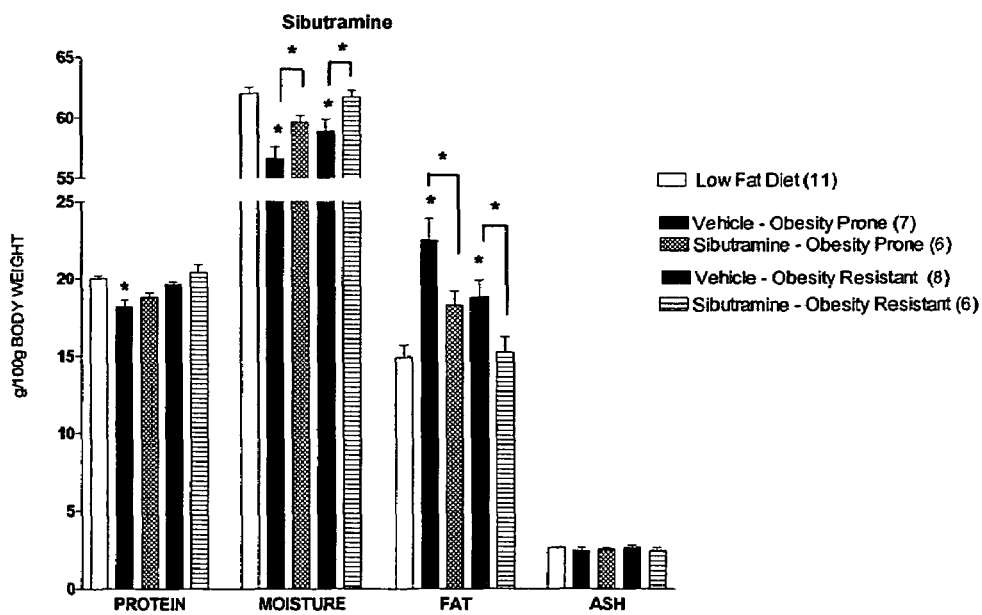
Figure 3A:
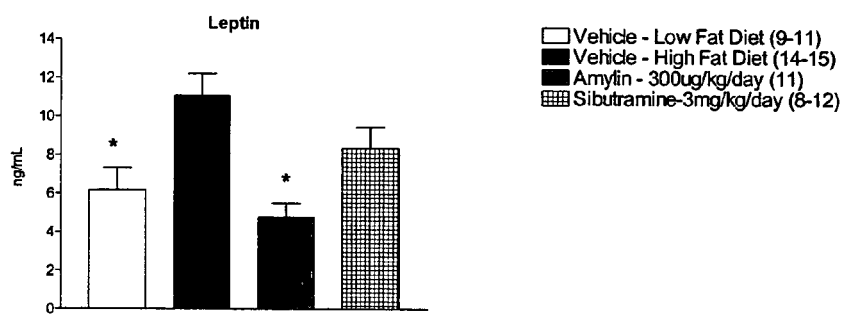
FIGS. 3A-3C, depict the leptin, insulin and triglycerides levels of DIO rats chronically administered amylin or sibutramine.
Figure 3B:
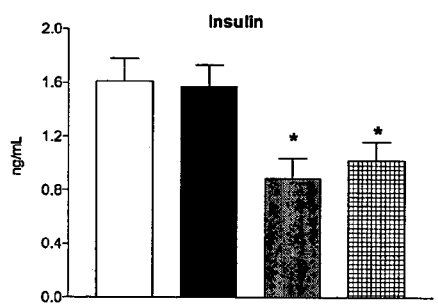
Figure 3C:
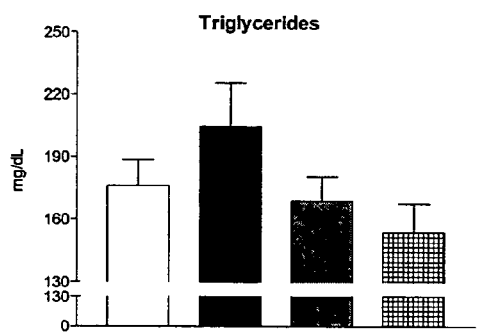

In this study, an obesity-prone/obesity-resistant difference in drug interaction was found for protein weight in amylin-treated rats, and thus body composition parameters were measured separately in obesity-prone and obesity-resistant animals in each drug group (FIGS. 2A and 2B). In obesity-prone rats, there was an increase in protein in the amylin-treated group when compared to the control group (vehicle only).

EXAMPLE 2

Figure 4A:
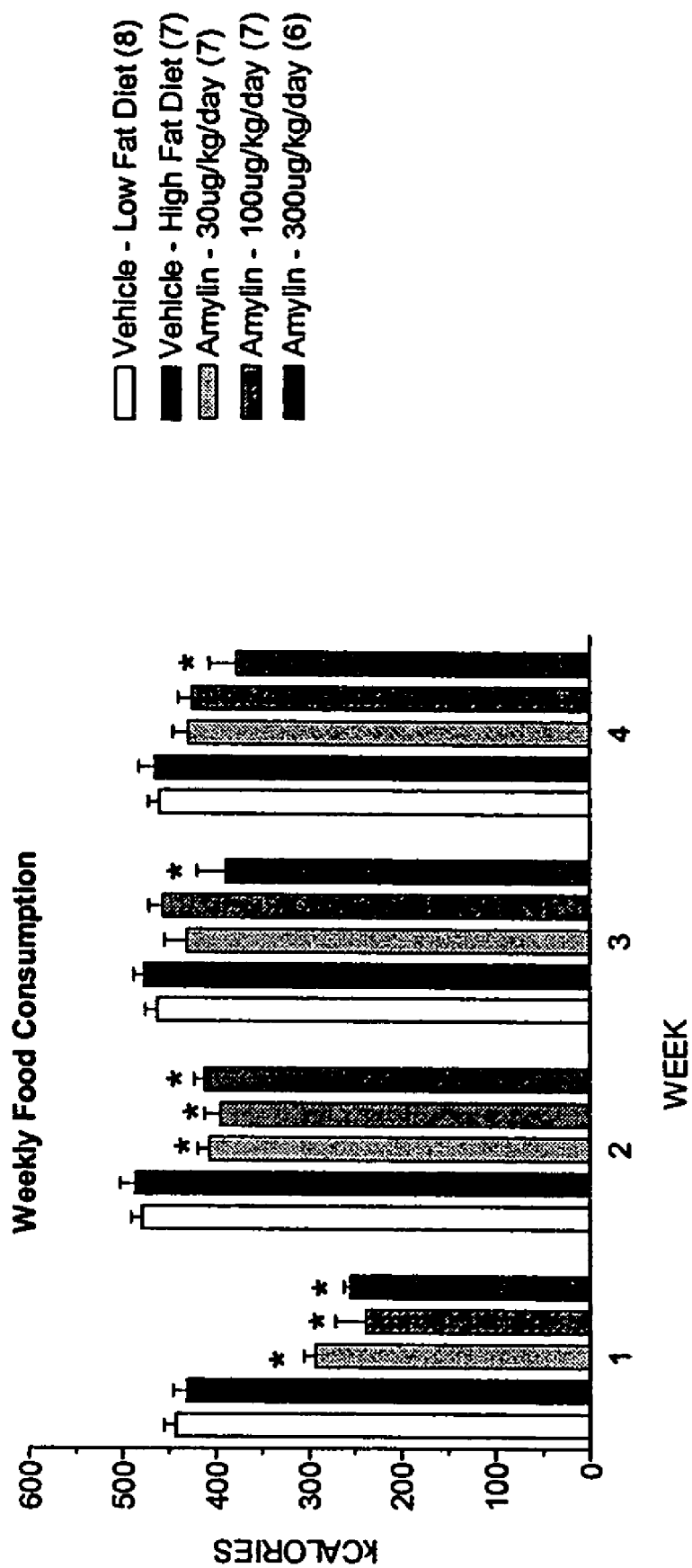
FIGS. 4A and 4B show the effects on food consumption and body weight, respectively, of three differing doses of amylin in DIO rats.
Figure 4B:
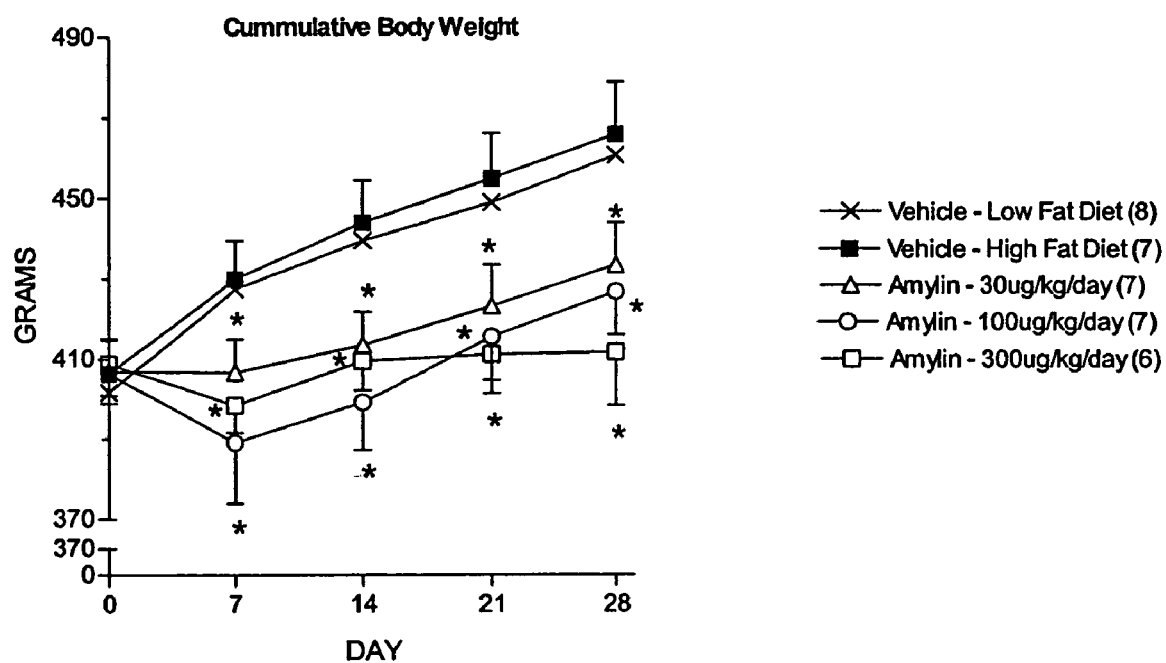
Figure 5:
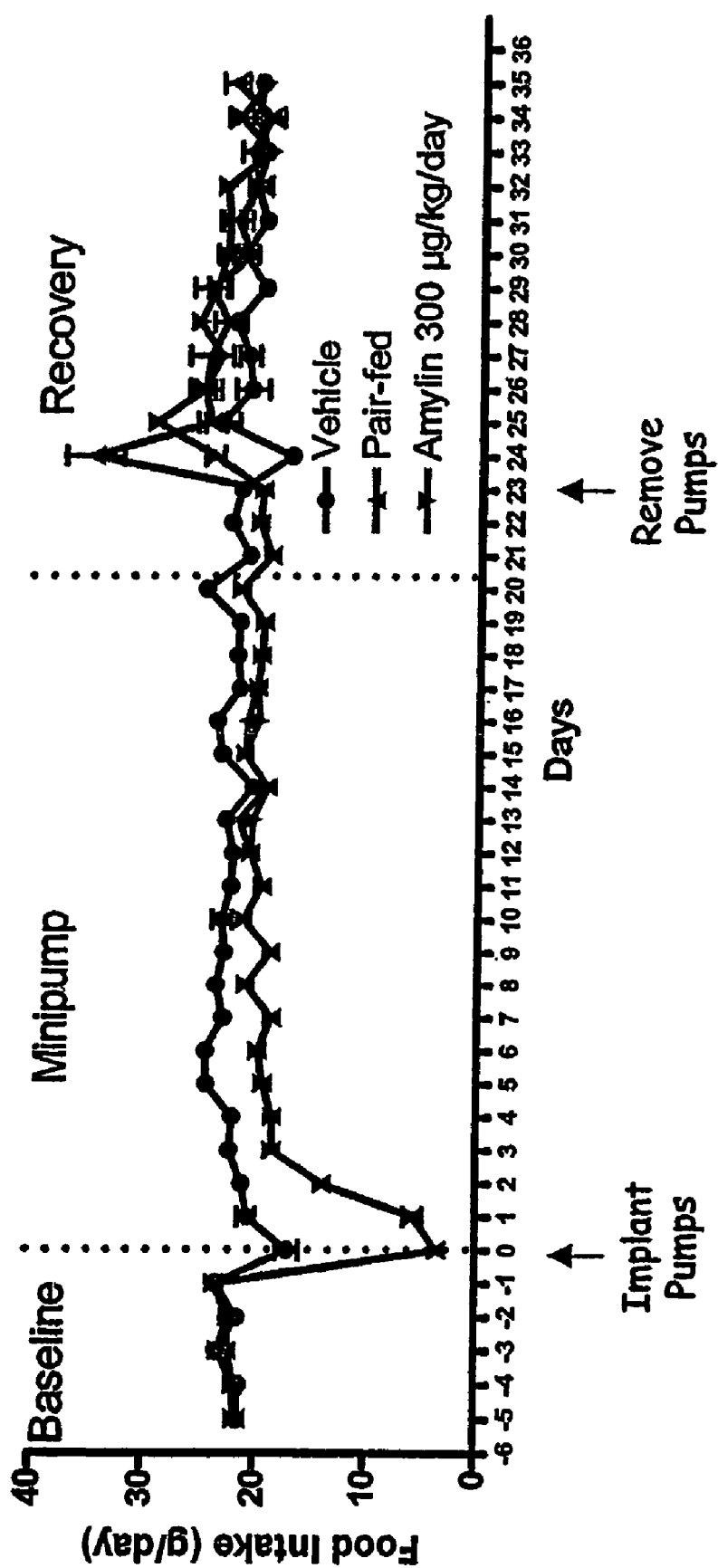
FIG. 5 depicts the effect of amylin on food intake in lean rats.
Figure 7:
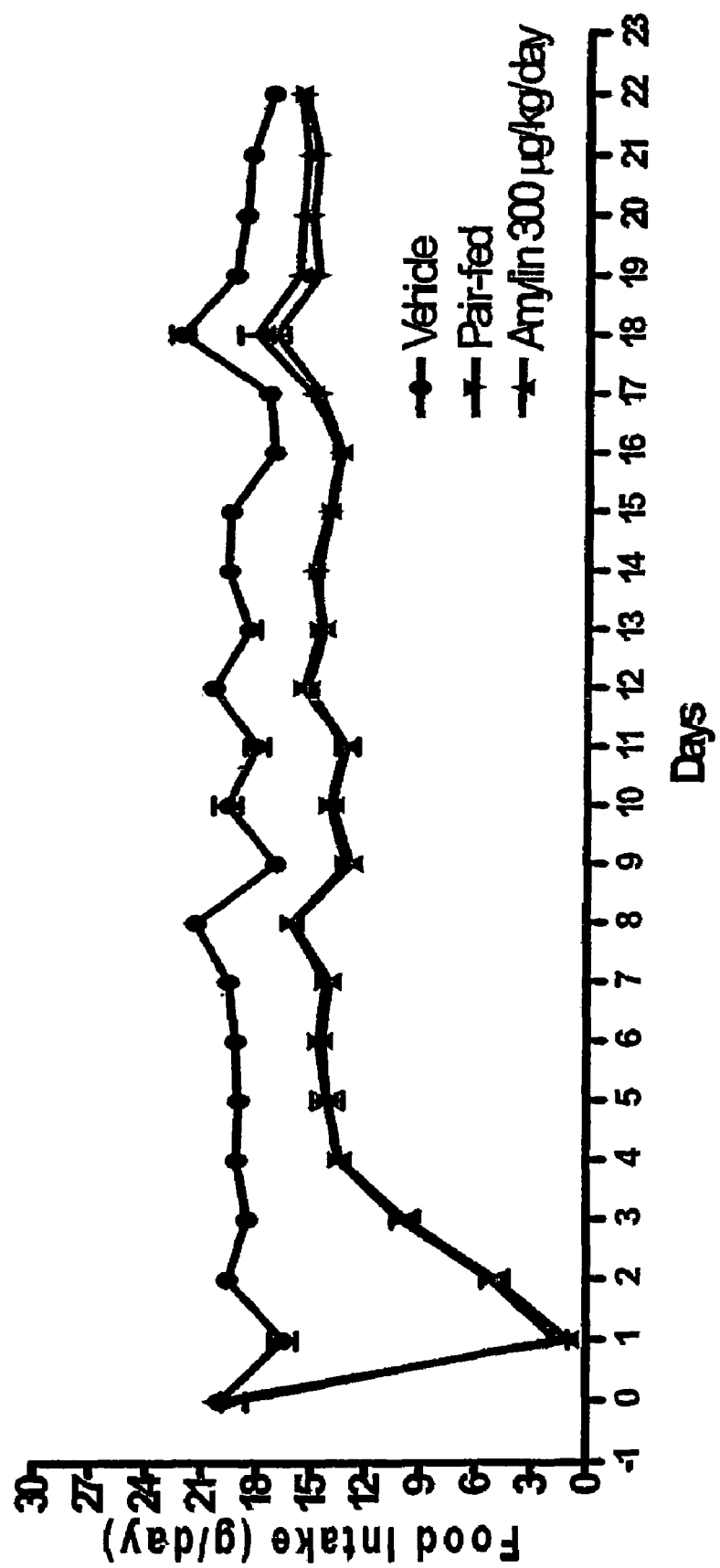
FIG. 7 depicts the effect of amylin on food intake in DIO Levin rats.
Figure 9A:
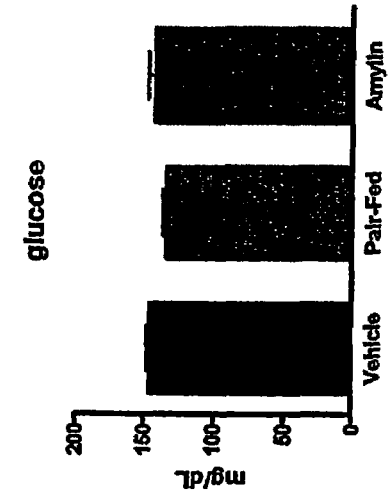
FIGS. 9A-9F depict the triglyceride, cholesterol, glucose, insulin, leptin, and liver triglyceride levels in lean rats chronically administered amylin.
Figure 9B:
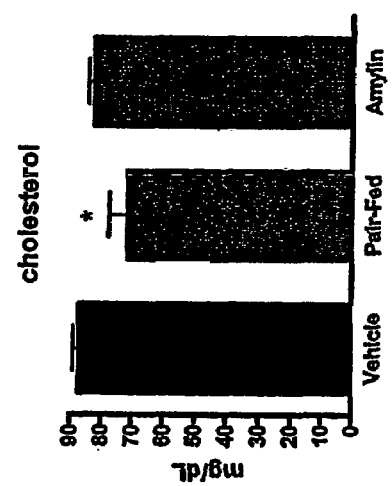
Figure 9C:
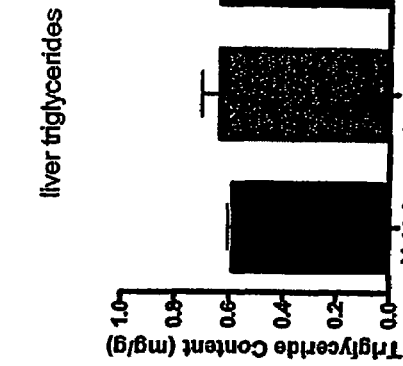
Figure 9D:
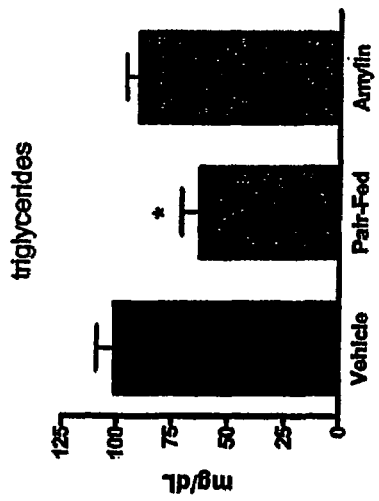
Figure 9E:
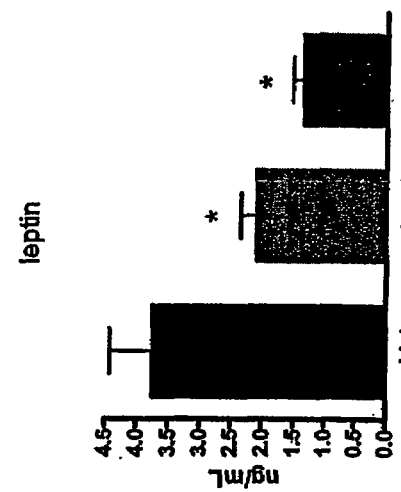
Figure 9F:
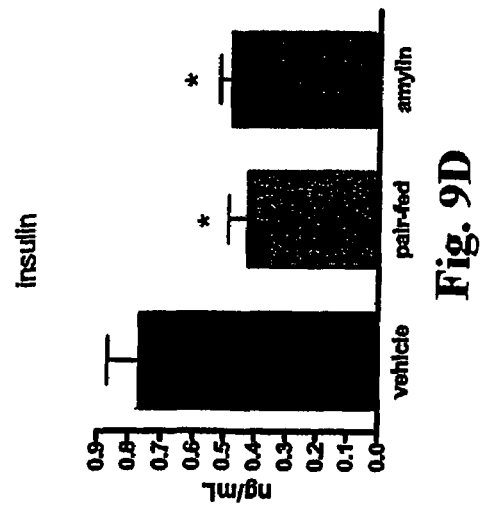
Figure 10C:
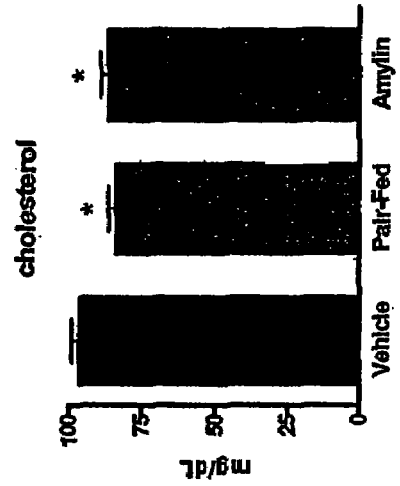
FIGS. 10A-10E depict the triglyceride, glucose, cholesterol, insulin, and leptin levels in DIO Levin rats chronically administered amylin.
Figure 10B:
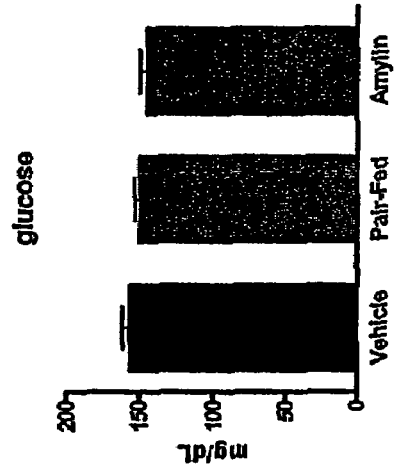
Figure 10A:
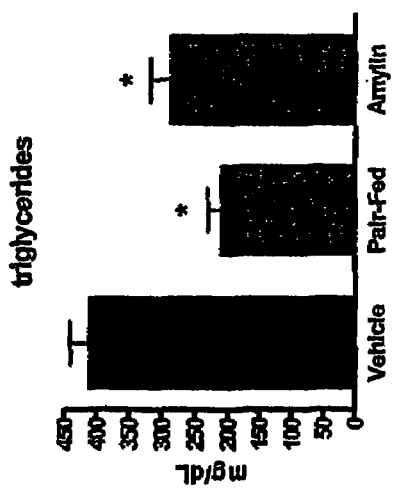
Figure 10E:
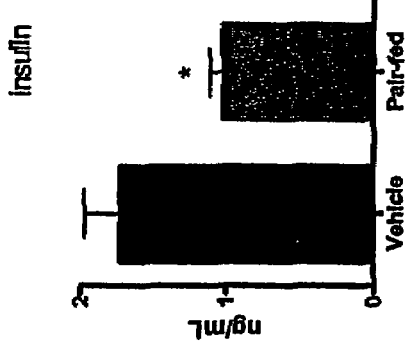
Figure 10D:
Figure 12A:
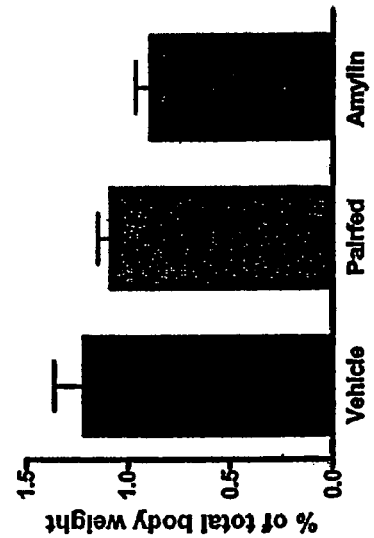
FIGS. 12A-12D depict the weight of selected fat pad as a percent of total body weight in DIO Levin rats chronically administered amylin.
Figure 12B:
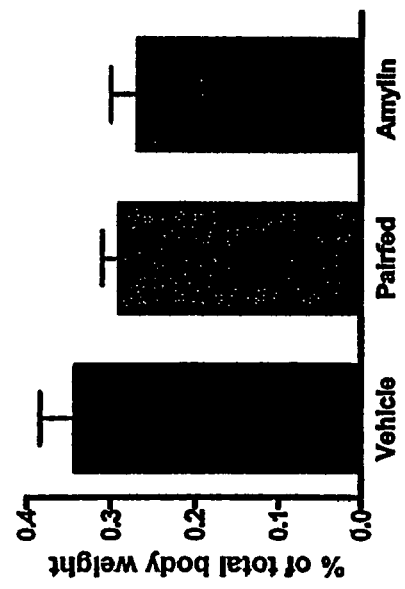
Figure 12C:
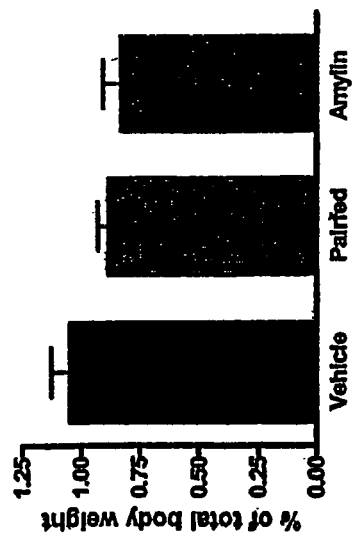
Figure 12D:
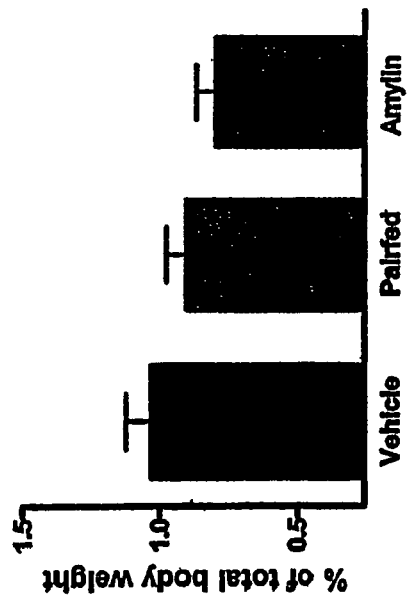

This experiment was similar to that of Example 1, except that the study group consisted of high fat-fed rats implanted with pumps delivering three doses of amylin (30, 100 and 300 µg/kg/day) or vehicle. Table 1B and FIGS. 4A and 4B show that the effects of amylin on food intake and body weight are dose-dependent, with a reduction in body weight gain being observed at 30 µg/kg/day.

TABLE 1B

| | 30 µg/kg/day amylin | | 100 µg/kg/day amylin | | 300 µg/kg/day amylin | |
|---|---|---|---|---|---|---|
| Week | Caloric Intake | Body Weight | Caloric Intake | Body Weight | Caloric Intake | Body Weight |
| 1 | 32%* | 5%* | 45%* | 10%* | 41%* | 7%* |
| 2 | 17%* | 7%* | 19%* | 10%* | 15%* | 8%* |
| 3 | 10% | 7%* | 4% | 9%* | 19%* | 10%* |
| 4 | 8% | 7%* | 9% | 8%* | 19%* | 12%* |

*P < 0.05, significantly different from high fat-fed controls.

EXAMPLE 3

Lean, male Harlan SPRAGLE DAWLEY® (HSD) (Harlan 7012) rats were maintained on "standard chow" (~5% calories from fat). DIO (Levin; Charles River) male rats were maintained on Research Diets' 12266B chow (17% protein, 51% carbohydrate, 32% fat) for 6 weeks prior to the experiment, resulting in a weight gain of ~150 to 200 g/animal.

Rats were implanted subcutaneously with 28-day osmotic pumps containing either amylin (300 mg/kg/day; synthesized at Amylin Pharmaceuticals, Inc.) or vehicle (50% DMSO; control and pair-fed groups). Food intake and body weight were recorded daily (FIGS. 5, 6A, 6B, 7, 8A, and 8B). While amylin and vehicle-control rats always had ad libitum access to food, intake in the pair-fed control group was restricted to the amount consumed by the amylin-treated group.

On the final day of the experiment, rats were deeply anaesthetized and sacrificed by cardiac puncture. Plasma triglycerides, glucose, and cholesterol were measured on a COBAS Mira plasma Analyzer (Roche). Plasma leptin and insulin were measured using Linco Research kits. (See, FIGS. 9A-9F and 10A-10E.) Body composition was measured by chemical analysis (Covance Laboratories, Madison, Wis.). Fat pad weights of the epididymal, retroperitoneal, subcutaneous, and perirenal fat pads (all unilateral; analysis only done in DIO animals) were carefully dissected and weighed (FIGS. 12A-12D). In analyzing the tissue biochemistry, triglycerides were powdered under liquid $N_2$ and extracted in chloroform: methanol. 0.6% NaCl solution was then added and the tubes were vortexed, centrifuged, and the organic phase was transferred to glass scintillation vials and dried under a stream of $N_2$. Dried lipids were resuspended and triglycerides were quantified by enzymatic assay (Pointe Scientific, Inc.). Tissue glycogen was measured by the amyloglucosidase method. (See FIGS. 11A-11D.)

All data are represented as mean±SEM. Analysis of variance (ANOVA) and Bonferroni post-hoc tests were used to test for group differences (SYSTAT® for Windows). A P-value <0.05 was considered significant. Graphs were generated using PRISM® 4 for Windows (Graphpad Software).

Results showed that amylin treatment and pair-feeding both induced a 12% reduction in body weight relative to vehicle controls in lean and DIO rats. Chronic infusion of amylin significantly changed body composition relative to pair-fed and/or vehicle animals.

Amylin-treated lean rats and pair-fed lean rats showed a significant reduction in weight gain compared to vehicle rats. Amylin-treated lean rats also had a lower percent body fat relative to pair-fed while the percent protein remained relatively constant, suggesting amylin may have a metabolic mechanism of action as well as the ability to reduce food intake.

TABLE 2

| | Vehicle | Pair-fed | Amylin |
|---|---|---|---|
| Weight (g) | 425.45 | 397.85* | 392.25* |
| Fat (%) | 8.3 ± 0.9 | 9.52 ± 1.2 | 7.2 ± 1.5† |
| Protein (%) | 20.72 ± 0.69 | 20.62 ± 1.07 | 20.67 ± 0.74 |
| Moisture (%) | 66.68 ± 0.7 | 66.27 ± 0.7 | 67.57 ± 0.7† |

*$P < 0.05$, compared to vehicle.
†$P < 0.05$, compared to pair-fed.

Amylin-treated DIO rats and pair-fed DIO rats showed a significant reduction in weight gain compared to vehicle rats.

Amylin-treated DIO rats also showed a significant decrease in percent body fat and a significant preservation or gain in percent protein. Again, this result suggests that amylin may have a metabolic as well as weight reducing effect.

TABLE 3

| | Vehicle | Pair-fed | Amylin |
|---|---|---|---|
| Weight (g) | 612.99 | 551.33* | 548.94* |
| Fat (%) | 33.4 ± 4.7 | 27.64 ± 5.7 | 24.3 ± 6.5* |
| Protein (%) | 15.61 ± 1.37 | 16.85 ± 1.53 | 18.09 ± 1.68* |
| Moisture (%) | 49.46 ± 2.6 | 53.93 ± 4.5 | 56.68 ± 4.4* |
| Ash (%) | 1.34 ± 0.26 | 1.81 ± 0.59 | 1.65 ± 0.34 |

*$P < 0.05$, compared to vehicle.

Also seen from this experiment is that reductions in body weight were not accompanied by alterations in liver or muscle triglycerides or in liver glycogen content. However, rats given amylin or pair-fed had significantly reduced muscle glycogen content. Further, reductions in body weight were generally accompanied by reductions in metabolites and plasma insulin and leptin.

EXAMPLE 4

In this experiment, the effect of prior or concurrent food restriction on the ability of amylin to effect weight loss was evaluated. Retired female breeder rats were maintained on a high fat diet (40% fat) for 8 weeks. Prior to drug treatment, rats were either ad-lib fed or food restricted to 95% of their starting body weight. The rats were then sub-divided into treatment groups that received either vehicle or amylin (100 μg/kg/day) and placed under either a restricted or ad-lib feeding schedule (8 groups total).

Figure 13:
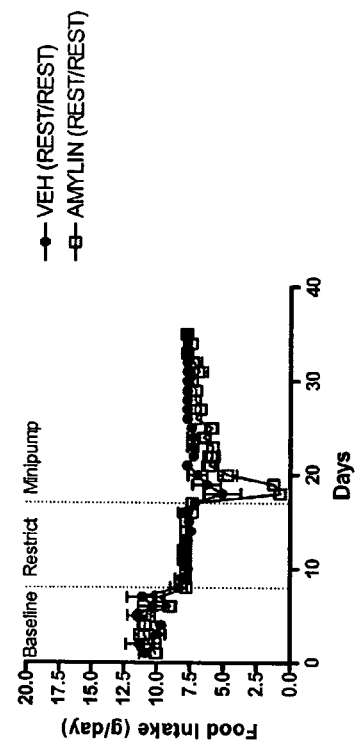
FIGS. 13A-13P depict the effect of amylin, in conjunction with prior or concurrent food restriction, on food intake, body weight and body composition in retired female breeder rats.
Figure 13:
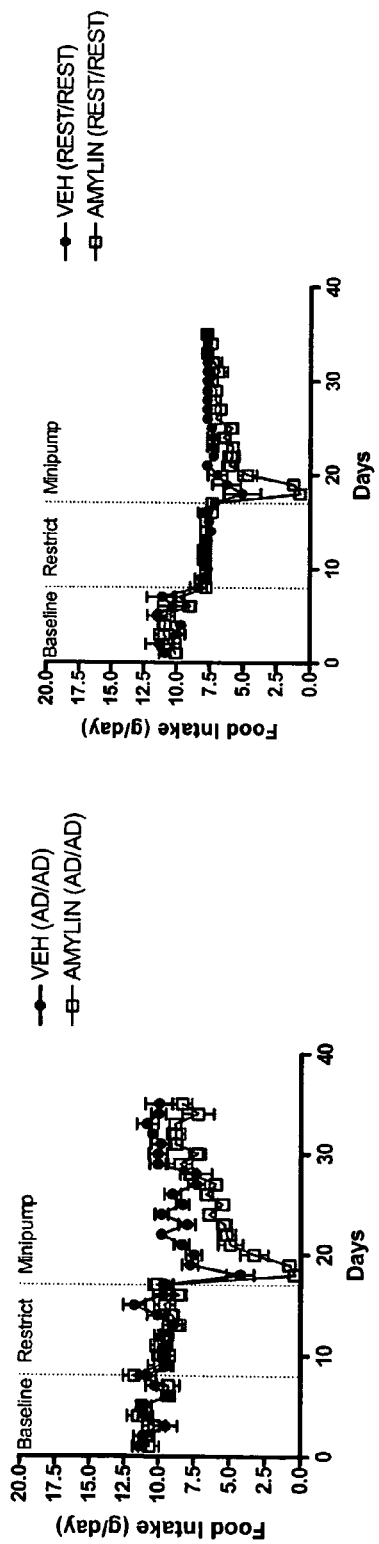
Figure 13:
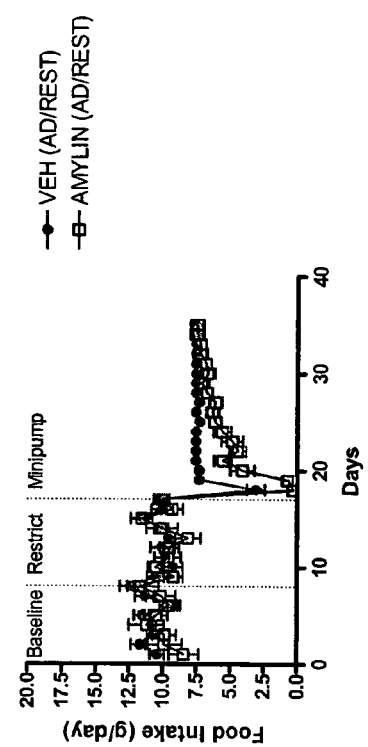
Figure 13:
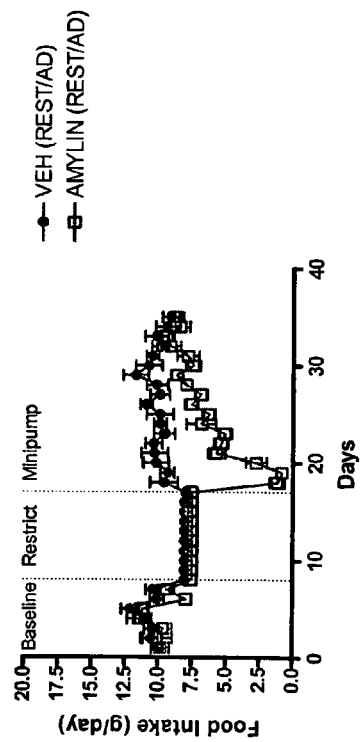
Figure 13:
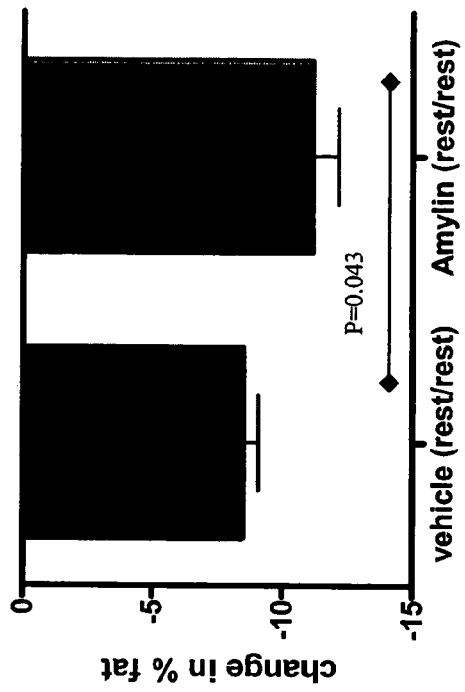
Figure 13:
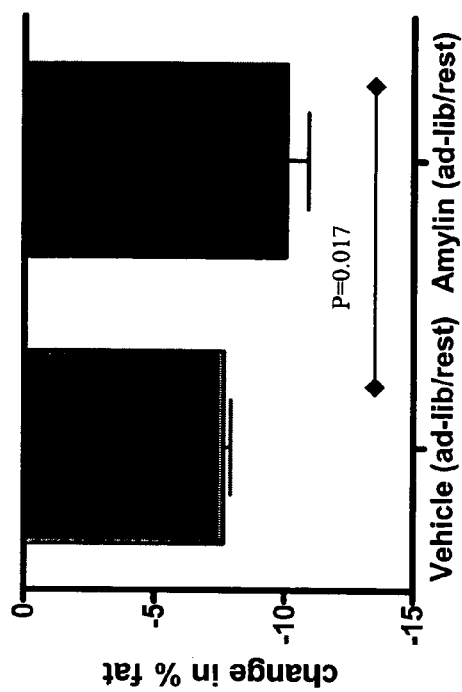
Figure 13:
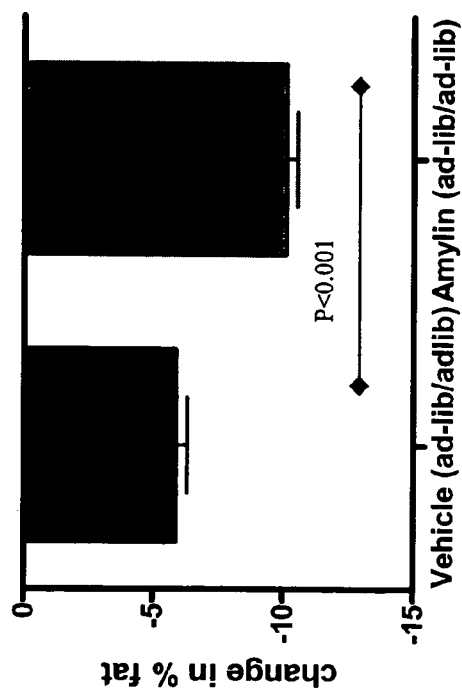
Figure 13:
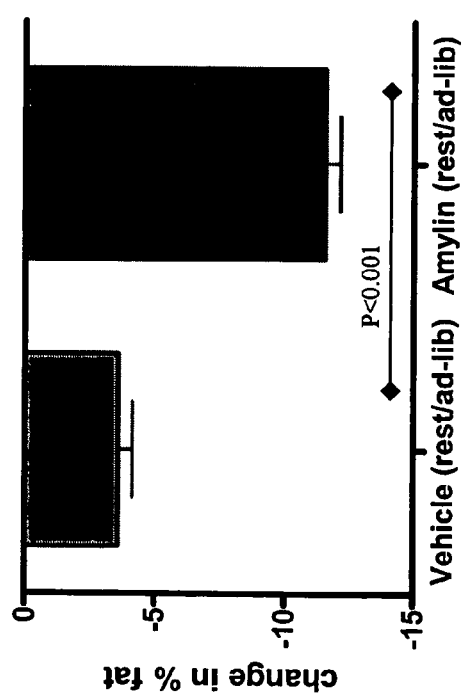
Figure 13:
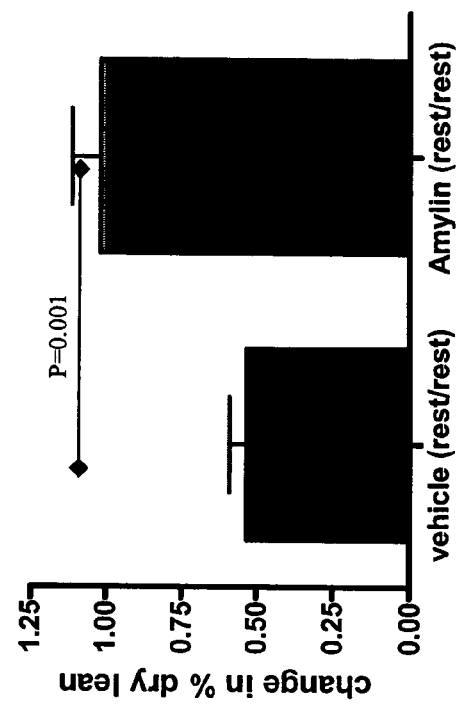
Figure 13:
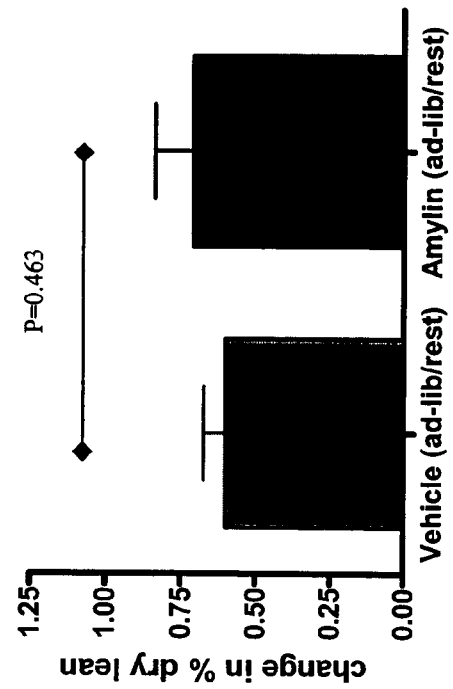
Figure 13:
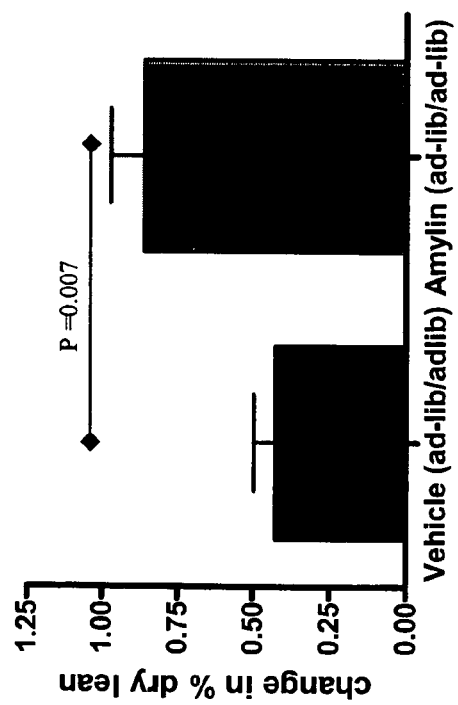
Figure 13:
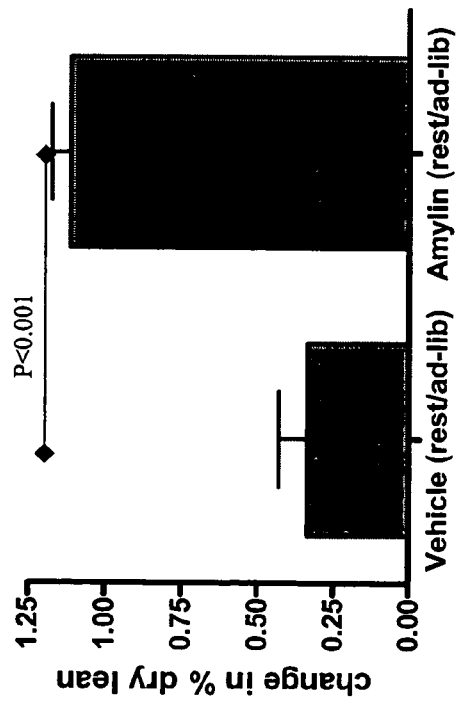
Figure 14A:
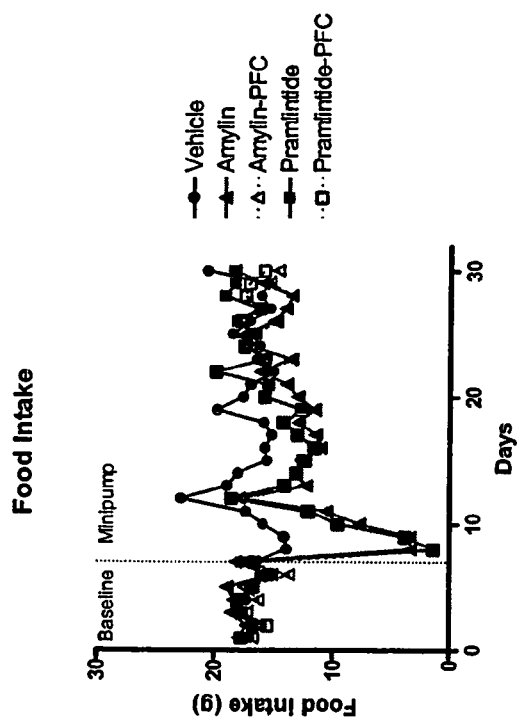
Figure 14B:
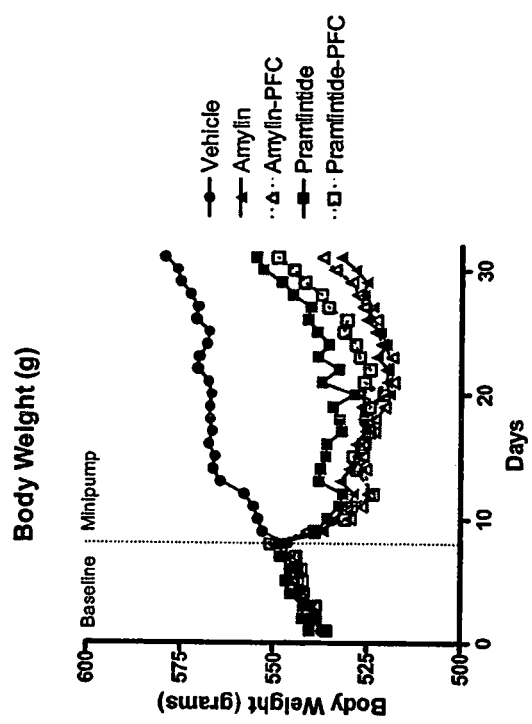
Figure 14F:
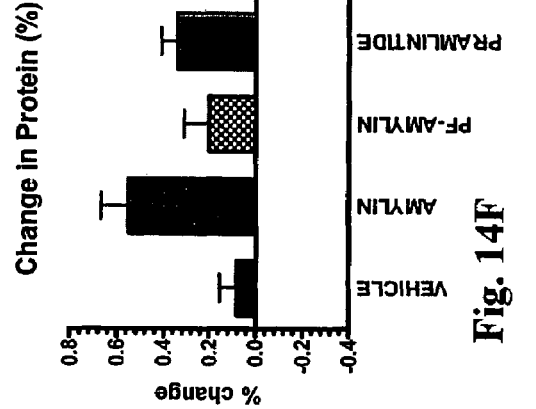
Figure 14H:
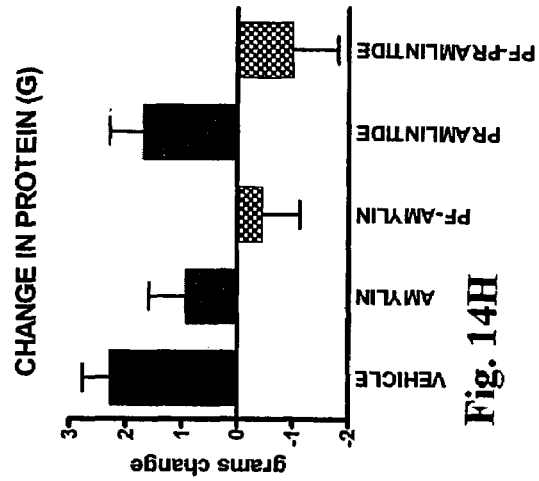
Figure 14E:
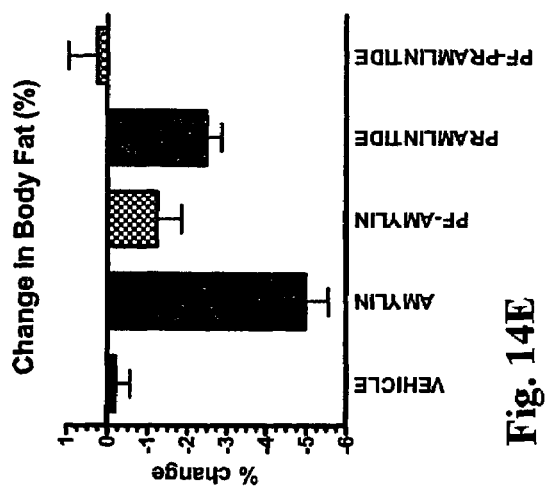
Figure 14G:
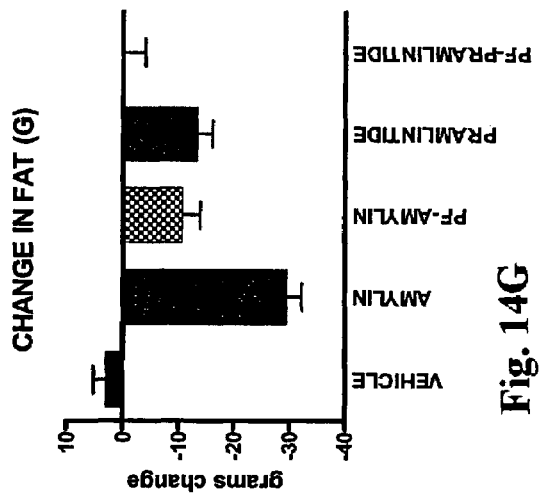

Changes in body weight and body composition are summarized in the table below and depicted in FIGS. 13A-13P. Amylin significantly reduced body weight under all treatment conditions. These changes in body weight were accompanied by significant decreases in percent body fat (except in chronically restricted animals—which approached statistical significance) and increases in percent protein (except in ad-lib fed then food restricted group). The ability of amylin to reduce body weight along with decreasing adiposity and/or preserving lean tissue can be extended to a variety of nutritive states in female rats.

TABLE 4

| Food access prior to treatment | Food access during treatment | Treatment (n) | Estimated Mean Weight change from treatment (g) | % Change in fat | % Change in protein |
|---|---|---|---|---|---|
| Ad-lib | Ad-lib | Vehicle (7) | −8.1 ± 1.4 | −5.9 ± 0.4 | 0.4 ± 0.1 |
| | | Amylin (7) | −21.8 ± 1.4 | −10.1 ± 0.5 | 0.8 ± 0.1 |
| | | | ($p < 0.001$)* | ($p < 0.001$)* | ($p = 0.007$)* |
| Restricted | Restricted | Vehicle (7) | −9.3 ± 2.1 | −8.5 ± 0.5 | 0.5 ± 0.1 |
| | | Amylin (8) | −17.1 ± 2.0 | −11.1 ± 1.0 | 1.0 ± 0.1 |
| | | | ($p = .021$)* | ($p = 0.043$) | ($p = 0.001$)* |
| Restricted | Ad-lib | Vehicle (8) | 3.5 ± 2.4 | −3.5 ± 0.6 | 0.3 ± 0.1 |
| | | Amylin (7) | −18.2 ± 2.5 | −11.5 ± 0.6 | 1.1 ± 0.1 |
| | | | ($p < 0.001$)* | ($p < 0.001$)* | ($p < 0.001$)* |
| Ad-lib | Restricted | Vehicle (7) | −12.5 ± 2.3 | −7.6 ± 0.3 | 0.5 ± 0.1 |
| | | Amylin (6) | −23.1 ± 2.3 | −9.9 ± 0.9 | 0.7 ± 0.1 |
| | | | ($p = 0.007$)* | ($p = 0.017$)* | ($p = 0.463$) |

*significant at 0.025 adjusted for the number of comparisons (one-tailed tests).

FIGS. 13A-13D depict the effect of amylin on body weight for each of the eight groups of rats. Amylin treated rats lost more weight than their vehicle treated counterparts. FIGS. 13E-13H depict the effect of amylin on food intake for each of the eight groups of rats. Amylin treated rats ate less than their vehicle treated counterparts. FIGS. 13I-13L depict the effect of amylin on body fat for each of the eight groups of rats. In general, amylin treated rats had a greater decrease in percent body fat than their vehicle treated counterparts. FIGS. 13M-13P depict the effect of amylin on dry lean mass for each of the eight groups of rats. In general, amylin treated rats had a greater increase in percent lean body mass than their vehicle treated counterparts.

EXAMPLE 5

This experiment looked at the effect of amylin versus the effect of pramlintide (an amylin analog) on rats and also in comparison to pair-fed rats.

48 DIO Levin rats (an in-bred model of diet induced obesity) were used in this study. The rats were divided into five treatment groups (vehicle, n=10; amylin, n=10; pair-fed to amylin, n=9; pramlintide, n=10; pair-fed to pramlintide, n=9). The rats were treated with equi-molar concentrations of pramlintide and amylin (76 nmol/kg/day or approximately 300 μg/kg/day) by osmotic mini-pump for 24 days. Food intake and body weight was measured daily. Vehicle, amylin and pramlintide-treated rats had ad-lib access to food during the study. The pair-fed groups were only allowed to consume the daily intakes of their respective drug-treated groups. For body composition, rats were scanned in a rodent NMR before treatment and after sacrifice (at the end of the study), allowing for the ability to calculate changes in carcass fat and protein (e.g., lean tissue). FIGS. 14A-14H depict results that show amylin and pramlintide having a significant effect on slowing body weight gain in this model and having favorable effects on body composition.

To assist in understanding the present invention, the following further Examples 7-9 are included and describe the results of a series of experiments therein. The following examples relating to this invention should not, of course, be construed as specifically limiting the invention. Such variations of the invention, now known or later developed, which would be within the purview of one skilled in the art are considered to fall within the scope of the present invention as hereinafter claimed.

EXAMPLE 7

Preparation of $^{25,28,29}$Pro-h-Amylin [SEQ ID NO:30]

Solid phase synthesis of $^{25,28,29}$Pro-h-amylin [SEQ ID NO:30] using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved, the resin and side chain protecting groups were cleaved with liquid HF in the presence of dimethylsulfide and anisole. The $^{25,28,29}$Pro-h-amylin [SEQ ID NO:30] was purified by preparative reversed-phase HPLC. The peptide was found to be homogeneous by analytical HPLC and capillary electrophoresis and the structure was confirmed by amino acid analysis and sequence analysis. The product gave the desired mass ion. FAB mass spec: $(M+H)^+$=3,949.

EXAMPLE 8

Receptor Binding Assay

Evaluation of the binding of compounds to amylin receptors was carried out as follows: $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200-250) grams were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GFB glass fiber filters (Whatman Inc., Clifton, N.J.) which had been presoaked for 4 hours in 0.3% polyethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds are set forth in Table I, showing that each of the compounds has significant receptor binding activity.

EXAMPLE 9

Soleus Muscle Assay

Evaluation of the amylin agonist activity of compounds was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The *tendo achilles* was cut just above *os calcis* and *m. gastrocnemius* reflected out from the posterior aspect of the tibia. *M. soleus*, a small 15-20 mm long, 0.5 mm thick flat muscle on the bone surface of *m. gastrocnemius* was then stripped clear and the perimysium cleaned off using fine scissors and forceps. *M. soleus* was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 15.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (Humulin-R, Eli Lilly, IN) and the test compound, as detailed below. pH at 37° C. was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37° C. in an oscillating water bath. After a half-hour "preincubation" period, 0.5 µCi of U—$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at −20° C. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in μmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, MD) to derive $EC_{50}$'S. Since $EC_{50}$ is log-normally distributed, it is expressed ± standard error of the logarithm. Pairwise comparisons were performed using t-test based routines of SYSTAT (Wilkinson, "SYSTAT: the system for statistics," SYSTAT Inc., Evanston, Ill. (1989)).

Dose response curves were generated with muscles added to media containing 7.1 nM (1000 μU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at −70° C.

Human amylin is a known hyperglycemic peptide, and $EC_{50}$ measurements of amylin preparations in the soleus muscle assay range typically from about 1-10 nM, although some commercial preparations which are less than 90% pure have higher $EC_{50}$'s due to the presence of contaminants that result in a lower measured activity. Results for test compounds are set forth in Table I, showing that each of the compounds has amylin activity.

TABLE 5

| | Receptor Binding | Soleus Muscle Assay $EC_{50}$(nM) |
|---|---|---|
| 1) $^{28}$Pro-h-Amylin [SEQ ID NO: 34] | 15.0 | 2.64 |
| 2) $^{25}$Pro$^{26}$Val$^{28,29}$Pro-h-Amylin [SEQ ID NO: 36] | 18.0 | 4.68 |
| 3) $^{2,7}$Cyclo-[$^{2}$Asp,$^{7}$Lys]-h-Amylin | 310.0 | 6.62 |
| 4) $^{2,37}$h-Amylin | 236.0 | 1.63 |
| 5) $^{1}$Ala-h-Amylin | 148.0 | 12.78 |
| 6) $^{1}$Ser-h-Amylin | 33.0 | 8.70 |
| 7) $^{29}$Pro-h-Amylin | 64.0 | 3.75 |
| 8) $^{25,28}$Pro-h-Amylin | 26.0 | 13.20 |
| 9) des-$^{1}$Lys$^{25,28}$Pro-h-Amylin | 85.0 | 7.70 |
| 10) $^{18}$Arg$^{25,28}$Pro-h-Amylin [SEQ ID NO: 32] | 32.0 | 2.83 |
| 11) des-$^{1}$Lys$^{18}$Arg$^{25,28}$Pro-h-Amylin [SEQ ID NO: 35] | 82.0 | 3.77 |
| 12) $^{18}$Arg$^{25,28,29}$Pro-h-Amylin [SEQ ID NO: 37] | 21.0 | 1.25 |
| 13) des-$^{1}$Lys$^{18}$Arg$^{25,28,29}$Pro-h-Amylin | 21.0 | 1.86 |
| 14) $^{25,28,29}$Pro-h-Amylin [SEQ ID NO: 30] | 10.0 | 3.71 |
| 15) des-$^{1}$Lys$^{25,28,29}$Pro-h-Amylin [SEQ ID NO: 39] | 14.0 | 4.15 |

While the foregoing description discloses the present invention, with examples provided for the purpose of illustration, it will be understood that the practice of the present invention encompasses all of the usual variations, adaptations, or modifications as being within the scope of the claimed invention.

The invention claimed is:

1. A method for reducing body fat or body fat gain in a subject, while maintaining or increasing lean body mass, comprising administering to the subject an amylin agonist comprising the structure of SEQ ID NO:5; thereby, reducing body fat or body fat gain while maintaining or increasing lean body mass.

2. The method of claim 1 wherein the subject is a mammal.

3. The method of claim 2 wherein the mammal is human.

4. The method of claim 3 wherein the human is overweight or obese.

5. The method of claim 1 wherein the amylin agonist is administered parentally.

6. The method of claim 1 wherein the body fat and lean body mass is percent body fat and percent lean body mass, respectively.

7. The method of claim 1 further comprising dieting.

* * * * *

SEQUENCE LISTING

<160> NUMBER OF SEQ ID NOS: 28

<210> SEQ ID NO 1
<211> LENGTH: 37
<212> TYPE: PRT
<213> ORGANISM: human

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 31
<212> TYPE: PRT
<213> ORGANISM: artificial
<220> FEATURE:
<223> OTHER INFORMATION: analog of amylin

<400> SEQUENCE: 2

Lys Cys Asn Thr Ala Thr Cys Ala Thr Gln Arg Leu Ala Asn Phe Leu
1               5                   10                  15

Val Arg Ser Ser Asn Asn Leu Thr Asn Val Gly Ser Asn Thr Tyr
            20                  25                  30

<210> SEQ ID NO 3
<211> LENGTH: 32
<212> TYPE: PRT

```
<213> ORGANISM: artificial
<220> FEATURE:
<223> OTHER INFORMATION: analog of amylin

<400> SEQUENCE: 3

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 4
<211> LENGTH: 32
<212> TYPE: PRT
<213> ORGANISM: artificial
<220> FEATURE:
<223> OTHER INFORMATION: analog of amylin

<400> SEQUENCE: 4

Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 5
<211> LENGTH: 32
<212> TYPE: PRT
<213> ORGANISM: artificial
<220> FEATURE:
<223> OTHER INFORMATION: analog of amylin

<400> SEQUENCE: 5

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 6
<211> LENGTH: 28
<212> TYPE: PRT
<213> ORGANISM: artificial
<220> FEATURE:
<223> OTHER INFORMATION: analog of amylin
<220> FEATURE:
<221> NAME/KEY: MOD_RES
<222> LOCATION: (1)..(1)
<223> OTHER INFORMATION: Isocap
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: FORMYLATION
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: FORMYLATION

<400> SEQUENCE: 6

Ser Thr Ala Val Leu Xaa Lys Leu Ser Gln Glu Leu Xaa Lys Leu Gln
1               5                   10                  15

Thr Tyr Pro Arg Thr Asn Thr Gly Ser Gly Thr Pro
            20                  25
```

<210> SEQ ID NO 7
<211> LENGTH: 37
<212> TYPE: PRT
<213> ORGANISM: artificial
<220> FEATURE:
<223> OTHER INFORMATION: analog of amylin

<400> SEQUENCE: 7

Lys Cys Asn Thr Ala Thr Cys Ala Thr Gln Arg Leu Ala Asn Ala Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 8
<211> LENGTH: 22
<212> TYPE: PRT
<213> ORGANISM: artificial
<220> FEATURE:
<223> OTHER INFORMATION: analog of amylin

<400> SEQUENCE: 8

Lys Cys Asn Thr Ala Thr Cys Ala Thr Ala Arg Leu Ala Ala Phe Leu
1               5                   10                  15

Ala Arg Ser Ser Gly Tyr
            20

<210> SEQ ID NO 9
<211> LENGTH: 37
<212> TYPE: PRT
<213> ORGANISM: artificial
<220> FEATURE:
<223> OTHER INFORMATION: analog of amylin

<400> SEQUENCE: 9

Lys Cys Asn Thr Ala Thr Cys Ala Thr Gln Arg Leu Ala Asn Phe Leu
1               5                   10                  15

Val His Ser Gly Asn Asn Phe Gly Ala Ile Leu Ser Ser Thr Asn Val
            20                  25                  30

Gly Ser Asn Thr Tyr
        35

<210> SEQ ID NO 10
<211> LENGTH: 18
<212> TYPE: PRT
<213> ORGANISM: artificial
<220> FEATURE:
<223> OTHER INFORMATION: analog of amylin

<400> SEQUENCE: 10

Cys Asn Thr Ala Thr Cys Ala Thr Ala Arg Leu Ala Ala Phe Leu Ala
1               5                   10                  15

Arg Ser

<210> SEQ ID NO 11
<211> LENGTH: 32
<212> TYPE: PRT
<213> ORGANISM: artificial
<220> FEATURE:
<223> OTHER INFORMATION: analog of amylin

<400> SEQUENCE: 11

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 12
<211> LENGTH: 32
<212> TYPE: PRT
<213> ORGANISM: artificial
<220> FEATURE:
<223> OTHER INFORMATION: analog of amylin

<400> SEQUENCE: 12

Lys Cys Asn Thr Ala Thr Cys Val Leu Gly Arg Leu Ser Gln Glu Leu
1               5                   10                  15

His Arg Leu Gln Thr Leu Pro Arg Thr Asn Thr Gly Ser Asn Thr Tyr
            20                  25                  30

<210> SEQ ID NO 13
<211> LENGTH: 32
<212> TYPE: PRT
<213> ORGANISM: artificial
<220> FEATURE:
<223> OTHER INFORMATION: analog of amylin

<400> SEQUENCE: 13

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 14
<211> LENGTH: 32
<212> TYPE: PRT
<213> ORGANISM: artificial
<220> FEATURE:
<223> OTHER INFORMATION: analog of amylin

<400> SEQUENCE: 14

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 15
<211> LENGTH: 32
<212> TYPE: PRT
<213> ORGANISM: artificial
<220> FEATURE:
<223> OTHER INFORMATION: analog of amylin

<400> SEQUENCE: 15

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 16
<211> LENGTH: 32
<212> TYPE: PRT
<213> ORGANISM: artificial
<220> FEATURE:
<223> OTHER INFORMATION: analog of amylin

```
<400> SEQUENCE: 16

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Gly Ser Asn Thr Tyr
            20                  25                  30

<210> SEQ ID NO 17
<211> LENGTH: 32
<212> TYPE: PRT
<213> ORGANISM: artificial
<220> FEATURE:
<223> OTHER INFORMATION: analog of amylin

<400> SEQUENCE: 17

Ala Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 18
<211> LENGTH: 32
<212> TYPE: PRT
<213> ORGANISM: artificial
<220> FEATURE:
<223> OTHER INFORMATION: analog of amylin

<400> SEQUENCE: 18

Lys Cys Ala Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 19
<211> LENGTH: 32
<212> TYPE: PRT
<213> ORGANISM: artificial
<220> FEATURE:
<223> OTHER INFORMATION: analog of amylin

<400> SEQUENCE: 19

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 20
<211> LENGTH: 32
<212> TYPE: PRT
<213> ORGANISM: artificial
<220> FEATURE:
<223> OTHER INFORMATION: analog of amylin

<400> SEQUENCE: 20

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 21
<211> LENGTH: 32
<212> TYPE: PRT
<213> ORGANISM: artificial
<220> FEATURE:
<223> OTHER INFORMATION: analog of amylin
```

```
<400> SEQUENCE: 21

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 22
<211> LENGTH: 28
<212> TYPE: PRT
<213> ORGANISM: artificial
<220> FEATURE:
<223> OTHER INFORMATION: analog of amylin
<220> FEATURE:
<221> NAME/KEY: MOD_RES
<222> LOCATION: (1)..(1)
<223> OTHER INFORMATION: Isocap

<400> SEQUENCE: 22

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 23
<211> LENGTH: 32
<212> TYPE: PRT
<213> ORGANISM: artificial
<220> FEATURE:
<223> OTHER INFORMATION: analog of amylin

<400> SEQUENCE: 23

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 24
<211> LENGTH: 32
<212> TYPE: PRT
<213> ORGANISM: artificial
<220> FEATURE:
<223> OTHER INFORMATION: analog of amylin

<400> SEQUENCE: 24

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 25
<211> LENGTH: 32
<212> TYPE: PRT
<213> ORGANISM: artificial
<220> FEATURE:
<223> OTHER INFORMATION: analog of amylin

<400> SEQUENCE: 25

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 26
```

```
<211> LENGTH: 32
<212> TYPE: PRT
<213> ORGANISM: artificial
<220> FEATURE:
<223> OTHER INFORMATION: analog of amylin

<400> SEQUENCE: 26

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 27
<211> LENGTH: 32
<212> TYPE: PRT
<213> ORGANISM: artificial
<220> FEATURE:
<223> OTHER INFORMATION: analog of amylin

<400> SEQUENCE: 27

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro
            20                  25                  30

<210> SEQ ID NO 28
<211> LENGTH: 32
<212> TYPE: PRT
<213> ORGANISM: artificial
<220> FEATURE:
<223> OTHER INFORMATION: analog of amylin

<400> SEQUENCE: 28

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Gly Thr Pro
            20                  25                  30
```